(12) United States Patent
Watanabe et al.

(10) Patent No.: US 7,732,426 B2
(45) Date of Patent: Jun. 8, 2010

(54) ISOCYCLOMALTOOLIGOSACCHARIDE (S), ISOCYCLOMALTOOLIGOSACCHARIDE-FORMING ENZYME, THEIR PREPARATION AND USES

(75) Inventors: Hikaru Watanabe, Okayama (JP); Tomoyuki Nishimoto, Okayama (JP); Michio Kubota, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 549 days.

(21) Appl. No.: 11/663,919

(22) PCT Filed: Sep. 26, 2005

(86) PCT No.: PCT/JP2005/017642

§ 371 (c)(1), (2), (4) Date: Mar. 27, 2007

(87) PCT Pub. No.: WO2006/035725

PCT Pub. Date: Apr. 6, 2006

(65) Prior Publication Data

US 2008/0131468 A1 Jun. 5, 2008

(30) Foreign Application Priority Data

Sep. 27, 2004 (JP) ............................. 2004-278971

(51) Int. Cl.
*A61K 31/715* (2006.01)
*A61K 31/702* (2006.01)
*C07H 1/00* (2006.01)

(52) U.S. Cl. ..................................... 514/54; 536/123.1
(58) Field of Classification Search ........................ None
See application file for complete search history.

(56) References Cited

U.S. PATENT DOCUMENTS

| 4,521,252 A | 6/1985 | Miyake et al. |
| 5,455,168 A | 10/1995 | Maruta et al. |
| 5,472,863 A | 12/1995 | Maruta et al. |
| 7,098,013 B2 | 8/2006 | Kubota et al. |
| 7,192,746 B2 | 3/2007 | Kubota et al. |
| 7,211,422 B2 | 5/2007 | Kubota et |
| 7,309,697 B2 * | 12/2007 | Mukai et al. ................. 514/61 |

FOREIGN PATENT DOCUMENTS

| GB | 2 106 912 A | 4/1983 |
| JP | 58-23799 A | 2/1983 |
| JP | 58-72598 A | 4/1983 |
| JP | 7-143876 A | 6/1995 |
| JP | 7-213283 A | 8/1995 |
| JP | 2005-095148 A | 4/2005 |
| WO | 01/90338 A1 | 11/2001 |
| WO | 02/040659 A1 | 5/2002 |
| WO | 02/055708 A1 | 7/2002 |
| WO | 2005/021564 A1 | 3/2005 |

OTHER PUBLICATIONS

French et al., "Studies of the Schardinger Dextrins. The Preparation and Solubility Characteristics of Alpha, Beta and Gamma Dextrins", Journal of American Cancer Society, vol. 71, pp. 353-358 (1949).
Hasegawa, Takeji, "Bisebutsu-No-Bunrui-To-Dotei" (Classification and Identification of Microorganisms), published by Japan Scientific Press, Tokyo, Japan (1985) (see p. 10 of the specification).
Sneath, Peter H., Bergey's Manual of Systematic Bacteriology, vol. 2, (1986).
"Handbook of Amylase and Related Enzymes", published by Pergamon Press Inc., Tokyo, Japan (1988).
Okada et al., "Digestion and Fermentation of Pullulan", Journal of Japanese Society of Nutrition and Food Sciences, vol. 43, No. 1, pp. 23-29 (1990).

* cited by examiner

*Primary Examiner*—Shaojia Anna Jiang
*Assistant Examiner*—Bahar Schmidtmann
(74) *Attorney, Agent, or Firm*—Browdy & Neimark, PLLC

(57) ABSTRACT

The present invention have objects to provide an option of non-reducing saccharide by providing a novel non-reducing saccharide composed of glucose as constituents and to provide a novel enzyme forming the non-reducing saccharide, a method and process for producing the same, a DNA encoding the enzyme, a recombinant DNA and transformant comprising the DNA, a composition comprising the non-reducing saccharide, and uses thereof. The present invention solves the above objects by providing an isocyclomaltooligosaccharide(s) having a structure represented by General Formula 1, a novel isocyclomaltooligosaccharide-forming enzyme, a method and process for producing the same, a DNA encoding the enzyme, a recombinant DNA and transformant comprising the DNA, a composition comprising the isocyclomaltooligosaccharide(s) or a saccharide composition comprising the same, and uses thereof.

$$\text{Cyclo}\{\rightarrow 6)\text{-}[\alpha\text{-D-Glcp-}(1\rightarrow 4)]_n\text{-}\alpha\text{-D-Glcp-}(1\rightarrow\} \quad \text{General Formula 1}$$

(In General Formula 1, "n" means a number of 4 or 5).

11 Claims, 8 Drawing Sheets

ISOCYCLOMALTOOLIGOSACCHARIDE (S), ISOCYCLOMALTOOLIGOSACCHARIDE-FORMING ENZYME, THEIR PREPARATION AND USES

TECHNICAL FIELD

The present invention relates to an isocyclomaltooligosaccharide(s) having a structure represented by General Formula 1 (hereinafter, may be simply abbreviated as "ICM" in this specification), ICM-forming enzyme, their preparation and uses. More particularly, the present invention relates to ICM having a structure represented by General Formula 1, ICM-forming enzyme, their preparation, a microorganism producing the enzyme, a DNA encoding the enzyme, a recombinant DNA comprising the DNA, a transformant, a method and process for producing ICM by using the enzyme, and a composition comprising ICM.

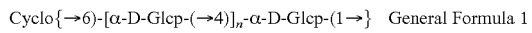

(In General Formula 1, "n" means a number of 4 or 5)

BACKGROUND ART

There have been known saccharides composed of glucose molecules as constituents, for example, partial starch hydrolyzates, produced from starches as materials, including amyloses, amylodextrins, maltodextrins, maltooligosaccharides, and isomaltooligosaccharides. Also, these saccharides are known to have usually non-reducing ends and reducing groups at their molecular ends and to exhibit reducing power. Usually, reducing power of partial starch hydrolyzates, on a dry solid basis, is represented by Dextrose Equivalent (DE). Partial starch hydrolyzates with high DE values are known to have a relatively low molecular weight, relatively low viscosity, strong sweetness and reactivity, easy reactivity with amino group-containing substances such as amino acids and proteins by amino carbonyl reaction that may induce browning and unpleasant smell and easily cause deterioration. In order to improve those disadvantages, methods for decreasing or eliminating the reducing power of partial starch hydrolyzates have been required for a long time. "*Journal of American Chemical Society*, Vol. 71, 353-358 (1949)" discloses a method to produce α-, β- or γ-cyclodextrin, constructed by 6, 7 or 8 glucose molecules bound by the α-1,4 glucosidic linkage, from starch by "macerans amylase". At present, these cyclodextrins are produced on an industrial scale and are applied to various uses because of their non-reducing power, tastelessness, and clathrating ability. Further, Japanese Patent Kokai Nos. 143,876/95 and 213,283/95, applied for by the same applicant as the present invention, disclose methods to convert maltooligosaccharides and partial starch hydrolyzates into trehalose, composed of two glucose molecules linked together via the α,α-1,1 linkage, by contacting them with a non-reducing saccharide-forming enzyme and a trehalose-releasing enzyme. At present, trehalose is produced from starch on an industrial scale and is applied to various uses because of its non-reducing power and its mild, high quality sweetness. While, International Patent Application Nos. WO 01/90338 A1, WO 02/055708 A1, and WO 02/40659 A1, applied for by the same applicant as the present invention, disclose methods to produce a cyclic tetrasaccharide, having a structure of binding four glucose molecules via alternating α-1,3 and α-1,6 glucosidic linkages, i.e., cyclo{→6)-α-D-glucopyranosyl-(1→3)-α-D-glucopyranosyl-(1→6)-α-D-glucopyranosyl-(1→3)-α-D-glucopyranosyl-(1→}, from starch or partial starch hydrolyzates by contacting them with α-isomaltosylglucosaccharide-forming enzyme and α-isomaltosyl-transferring enzyme. Further, Japanese Patent Kokai No. 2005-95148, applied for by the same applicant as the present invention, discloses a method to produce a cyclic tetrasaccharide, having a structure of binding four glucose molecules via alternating α-1,4 and α-1,6 glucosidic linkages, i.e., cyclo{→6)-α-D-glucopyranosyl-(1→4)-α-D-glucopyranosyl-(1→6)-α-D-glucopyranosyl-(1→4)-α-D-glucopyranosyl-(1→} (alias "Cyclic maltosylmaltose"), from starch or partial starch hydrolyzates by contacting them with cyclic maltosylmaltose-forming enzyme. These cyclic tetrasaccharides have abilities of clathrating other substances because of these cyclic structure, and stabilizing volatile organic substances. Further, since these saccharides have no reducing power, these are expected to be used and processed without causing browning and deterioration by amino-carbonyl reaction.

As described above, α-, β- or γ-cyclodextrin having a glucose polymerization degree of 6, 7 or 8, trehalose having a glucose polymerization degree of 2, a cyclic tetrasaccharide having a structure of cyclo{→6)-α-D-glucopyranosyl-(1→3)-α-D-glucopyranosyl-(1→6)-α-D-glucopyranosyl-(1→3)-α-D-glucopyranosyl-(1→} and a cyclic tetrasaccharide having a structure of cyclo{→6)-α-D-glucopyranosyl-(1→4)-α-D-glucopyranosyl-(1→6)-α-D-glucopyranosyl-(1→4)-α-D-glucopyranosyl-(1→} (alias "Cyclic maltosylmaltose"), are used in various fields on the basis of these respective advantages as non-reducing saccharides composed of glucose molecules. While, if other non-reducing saccharides distinct from the above saccharides would be provided, we would have more choice of using non-reducing saccharides, and application thereof for various uses can be expected.

DISCLOSURE OF INVENTION

Objects of the present invention are to provide an option of non-reducing saccharide by providing a novel non-reducing saccharide composed of glucoses as constituents and to provide a novel enzyme forming the non-reducing saccharide, a method and process for producing them, a DNA encoding the enzyme, a recombinant DNA and transformant comprising the DNA, a composition comprising the non-reducing saccharide, and uses thereof.

To solve the above objects, the present inventors have extensively screened microorganisms capable of producing a novel non-reducing saccharide-forming enzyme which forms a novel non-reducing saccharide when allowed to act on partial starch hydrolyzates. As a result, the present inventors isolated a novel microorganism of the genus *Bacillus*, named "AM7", from a soil in Okayama-city, Okayama, Japan, and found that the microorganism produces a novel enzyme which forms a remarkable amount of a novel isocyclomaltooligosaccharides (ICM) having a structure represented by General Formula 1, when allowed to act on α-1,4 glucans such as starches and partial hydrolyzates thereof. The present inventors also revealed the properties of the ICM-forming enzyme and established the process for producing the enzyme. The present inventors also established a DNA encoding the enzyme, a recombinant DNA comprising the DNA, a transformant, a method for forming ICM using the enzyme, and a process for producing ICM and a saccharide composition comprising the same by using the enzyme.

Cyclo{→6)-[α-D-Glcp-(1→4)]$_n$-α-D-Glcp-(1→} General Formula 1

(In General Formula 1, "n" means a number of 4 or 5)

The present invention solves the above objects by providing novel ICM having a structure represented by General Formula 1, a novel ICM-forming enzyme, a method and process for producing them, a DNA encoding the enzyme, a recombinant DNA and transformant comprising the DNA, a composition comprising ICM or a saccharide composition comprising the same, and uses thereof.

According to the present invention, an option of non-reducing saccharide composed of glucoses as constituents can be extended. Further, the present invention enables the provision of ICM, novel cyclic saccharides which have been ever unknown, in a large scale and the use of ICM in a various fields including foods and beverages, cosmetics, and pharmaceuticals.

Figure 1:
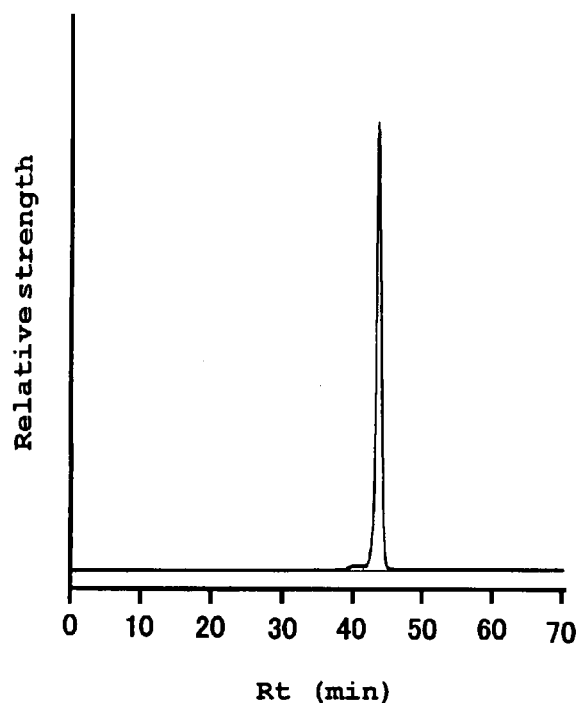
FIG. 1 shows the HPLC elution pattern of the preparation of Saccharide I.

In the figure, a section indicated with black bold line is a DNA encoding ICM-forming enzyme of the present invention, derived from *Bacillus circulans* AM7 (FERM BP-10111).

EXPLANATION OF SYMBOLS a: Glucose residue bound via the α-1,4 glucosidic linkage by hydroxyl group at the C-1 position
b: Glucose residue bound via the α-1,6 glucosidic linkage by hydroxyl group at the C-1 position

BEST MODE FOR CARRYING OUT THE INVENTION

Isocyclomaltooligosaccharide (ICM) as referred to as in the present invention means a cyclic saccharide having a structure represented by General Formula 1.

Cyclo{→6)-[α-D-Glcp-(1→4)]$_n$-α-D-Glcp-(1→} General Formula 1

(In General Formula 1, "n" means a number of 4 or 5)

Examples of ICM include ICM whose n in above General Formula is 4, i.e., a cyclic pentasaccharide having a structure that the C-1 hydroxyl group of the reducing end glucose of maltopentaose molecule forms the α-1,6 glucosidic linkage with the C-6 hydroxyl group of the non-reducing end glucose of the same molecule (throughout the specification, abbreviated as "isocyclomaltopentaose" or "ICG$_5$"); and ICM whose n in above General Formula 1 is 5, i.e., a cyclic hexasaccharide having a structure that the C-1 hydroxyl group of the reducing end glucose of maltohexaose molecule forms the α-1,6 glucosidic linkage with the C-6 hydroxyl group of the non-reducing end glucose of the same molecule (throughout the specification, abbreviated as "isocyclomaltohexaose" or "ICG$_6$") are present as ICM.

These saccharides are novel and ever unknown saccharides, firstly found in a culture medium of a microorganism isolated from a soil by the present inventors. The present invention encompasses cyclic pentasaccharide and cyclic hexasaccharide constructed by glucoses independently of by those source, form, purity, and process for producing, as far as they have the above mentioned structure.

ICM-Forming enzyme as referred to as in the present invention means any enzyme which catalyzes the following reactions:

Acting on α-1,4 glucan having a glucose polymerization degree of 3 or higher as substrate and forming various maltooligosaccharides different in glucose polymerization degree by catalyzing intermolecular α-1,4 transglycosylation transferring a series of maltooligosaccharides to C-4 hydroxyl group of the non-reducing end glucose of α-1,4 glucan (disproportionation reaction).

In the case of acting on α-1,4 glucan having a glucose polymerization degree of 7 (maltoheptaose), hydrolyzing the substrate by a maltopentaose unit from the non-reducing end of the substrate and catalyses a cyclization reaction, intramolecularly transferring the C-1 position of the reducing end glucose of maltopentaose to the C-6 hydroxyl group of non-reducing end glucose of the same maltopentaose to form ICG$_5$.

In the case of acting on α-1,4 glucans having glucose polymerization degrees of 8 or higher, hydrolyzing the substrate by a maltopentaose or maltohexaose unit from the non-reducing end of the substrate and catalyses a cyclization reaction, intramolecularly transferring the C-1 position of the reducing end glucose of maltopentaose or maltohexaose to the C-6 hydroxyl group of non-reducing end glucose of the same maltopentaose or maltohexaose to form ICG$_5$ and ICG$_6$.

ICM-forming enzyme of the present invention encompasses any enzyme catalyzing the above reaction without being restricted by its source, form, and purity.

The enzyme activity of ICM-forming enzyme of the present invention can be assayed as follows: A substrate solution is prepared by dissolving amylose in 50 mM acetate buffer (pH 6.0) containing 1 mM CaCl$_2$ to give a concentration of 1.25% (w/v). 0.2 ml of an enzyme solution is added to 0.8 ml of the substrate solution, and the mixture solution is incubated at 30° C. for 30 min. After stopping the reaction by heating at about 100° C. for 10 min, the reaction mixture is admixed with 4,000 units/g-solid of α-glucosidase and 250 units/g-solid of glucoamylase to hydrolyze the remaining soluble starch and concomitant oligosaccharides, and followed by the enzyme treatment at 50° C. for one hour. The amount of ICG$_5$ contained in the treated mixture is determined by HPLC described later in Experiment 1. One unit activity of ICM-forming enzyme is defined as the amount of enzyme which forms one μmole of ICG$_5$ per minute under the above conditions.

As a concrete example of ICM-forming enzyme of the present invention, the enzyme having the following physicochemical properties can be listed.
(1) Molecular Weight
   106,000±20,000 daltons when determined on SDS-gel electrophoresis;
(2) Isoelectric Point
   pI 7.5±0.5 on isoelectrofocusing Ampholine®, a carrier ampholyte;
(3) Optimum Temperature
   50 to 55° C. when reacted at pH 6.0 for 30 min;
(4) Optimum pH
   pH 4.5 to 8.0 when reacted at 30° C. for 30 min;
(5) Thermal Stability
   Stable up to 35° C. when incubated at pH 6.0 for 60 min
   Stable up to 40° C. in the presence of 1 mM $Ca^{2+}$ ion; and
(6) pH Stability
   Stable in a pH range of 4.5 to 9.0 when incubated at 4° C. for 24 hours;

One of ICM-forming enzyme of the present invention, having the above physicochemical properties, may have an amino acid sequence of SEQ ID NO:1 as the N-terminal amino acid sequence.

Usually, ICM-forming enzyme of the present invention has a prescribed amino acid sequence. For example, an amino acid sequence of SEQ ID NO:2 or those homologous to SEQ ID NO:2 can be listed. A variant enzyme having an amino acid sequence homologous to SEQ ID NO:2 means an enzyme having an amino acid sequence where one or more amino acids in SEQ ID NO:2 are deleted, replaced or added with other amino acids without altering the enzyme activity of acting on α-1,4 glucan having a glucose polymerization degree of 3 or higher and forming ICM represented by General Formula 1. As such a variant enzyme, it is preferable that the enzyme has an amino acid sequence with a homology to SEQ ID NO:2 of, usually, 60% or higher, desirably, 70% or higher, more desirably, 80% or higher, and most desirably, 90% or higher.

However, ICM-forming enzyme, having the physicochemical properties or any of the amino acid sequences described above, is just an example. ICM-forming enzyme of the present invention includes any enzyme having different physicochemical properties or N-terminal amino acid sequences from the above ones, as long as it produces ICM.

Although ICM-forming enzyme of the present invention is not restricted by its source, bacteria, particularly, the bacterial strain AM7 isolated from a soil by the present inventors can be preferably used as the source. The following are the identification results of the strain AM7 capable of producing ICM-forming enzyme. The identification of the strain AM7 was carried out according to the method as described in "*BISEIBUTSU-NO-BUNRUI-TO-DOTEI*" (Classification and Identification of Microorganisms), edited by Takeji Hasegawa, published by Japan Scientific Societies Press, Tokyo, Japan (1985).

<A. Morphology>
   (1) Characteristic of cells when incubated at 27° C. in nutrient agar;
      Existing usually in a rod shape of 0.5×2 to 0.7×5 μm,
      Gram stain, positive,
      Possessing motility,
      Exhibiting oval spores, and
      Forming swollen sporangium at the end of cell <B. Cultural Property>
   (1) Characteristics of colony formed when incubated at 27° C. in nutrient agar plate;
      Shape: Circular colony having a diameter of 1-2 mm after 3 days incubation
      Rim: Entire
      Projection: Flattened shape
      Gloss: Dull
      Surface: Rough
      Color: Opaque and white
   (2) Characteristics of colony formed when incubated at 27° C. in nutrient agar slant;
      Growth: Medium
      Shape: Thread-like <C. Physiological Properties>
   (1) VP-test: Negative
   (2) Catalase: Positive
   (3) Hydrolysis of starch: Positive
   (4) Decomposition of tyrosine: Negative
   (5) Deamination of phenylalanine: Negative
   (6) Reduction of nitrate: Positive
   (7) Formation of acids: Forming acids from D-glucose, L-arabinose, D-xylose, and D-mannitol
   (8) Growth conditions: Growing at a pH of 5.7-9.8, a temperature of 10 to 37° C., and NaCl concentration of 0-2%
   (9) Oxygen requirements: Facultative anaerobic, and
   (10) Mol % of guanine (G) plus cytosine (C) of DNA: 50.7% The bacteriological properties were compared with those of known microorganisms with reference to Bergey's Manual of Systematic Bacteriology, Vol. 2 (1986). As a result, it was revealed that the microorganism was identified as of *Bacillus circulans*. Based on these results, the present inventors named this microorganism "*Bacillus circulans* AM7" and deposited it on Aug. 25, 2004, in International Patent Organism, National Institute of Advanced Industrial Science and Technology, AIST Tsukuba Central 6, 1-1, Higashi 1-Chome Tsukuba-shi, Ibaraki-ken Japan, and accepted under the accession number of FERM BP-10111.

In addition to the above mentioned microorganism and its mutant, a microorganism capable of producing ICM-forming enzyme of the present invention includes other microorganisms and their mutants, capable of producing ICM-forming enzyme.

The term "the DNA of the present invention" means any DNA encoding the above mentioned ICM-forming enzyme. The DNA of the present invention includes any of a DNA originated from the nature and those which are synthesized artificially as far as they encode ICM-forming enzyme. Microorganisms of the genus *Bacillus*, including *Bacillus circulans* AM7 (FERM BP-10111) can be used as the natural sources of the DNA. A genomic DNA containing the DNA of the present invention can be obtained from the cells of these microorganisms. Specifically, a genomic DNA containing the DNA can be released extracellularly by the steps of inoculating any of the microorganisms into a nutrient medium, culturing about one to three days under aerobic conditions, collecting the cells from the culture, and treating the cells with cell-lytic enzymes such as lysozyme and β-glucanase or with ultrasonication. In addition to the methods described above, use of protein-hydrolyzing enzymes such as proteinases, detergents such as SDS, and freeze-thaw method are also applicable. The objective DNA can be obtained from the cells treated by using conventional methods in the art, for example, such as phenol-extraction, alcohol-precipitation, centrifugation, and ribonuclease-treatment. To artificially synthesize the DNA of the present invention, it can be chemically synthesized based on the amino acid sequence of SEQ ID NO:2. PCR-Method is also applicable to obtain the DNA by using a genomic DNA containing the DNA as a template and an appropriate chemically synthetic DNA as a primer.

The DNA of the present invention has, usually, a prescribed nucleotide sequence, for example, a nucleotide sequence of SEQ ID NO:3 or a nucleotide sequence homologous to SEQ ID NO:3. A variant DNA, having a homologous nucleotide sequence to SEQ ID NO:3, means that having a nucleotide sequence where one or more nucleotides in SEQ ID NO:3 are deleted, replaced or added with other nucleotides without altering the activity of the enzyme encoded thereby. The homology of nucleotide sequence to SEQ ID NO: 3 of such a variant DNA is preferable to be, usually, 60% or higher, desirably, 70% or higher, more desirably, 80% or higher, and most desirably, 90% or higher. The DNA of the present invention encompasses a DNA having a nucleotide sequence where one or more nucleotides of SEQ ID NO: 3 are replaced with other nucleotides without altering the encoded amino acid sequence based on the degeneracy of genetic code.

The DNA of the present invention can be advantageously used for constructing a recombinant DNA by inserting to an appropriate self-replicable vector. Recombinant DNAs are usually constructed by a DNA and a self-replicable vector, and they can be relatively easily prepared by conventional recombinant DNA techniques if the DNAs are obtained. Such vectors include, for example, plasmid vectors such as pBR322, pUC18, pBluescript II SK(+), pUB110, pTZ4, pC194, pHV14, TRp7, YEp7 and pBS7; and phage vectors such as λgt·λC, λgt·λB, ρ11, φ1 and φ105. To express the DNA of the present invention in $E.\ coli$, pBR322, pUC18, pBluescript II SK(+), λgt·λC and λgt·λB can be preferably used. While, to express the DNA of the present invention in $Bacillus\ subtilis$, pUB110, pTZ4, pC194, ρ11, φ1 and φ105 can be preferably used. Plasmids, pHV14, TRp7, YEp7 and pBS7 are useful in the case of replicating the recombinant DNA in two or more kinds of hosts. In order to insert a DNA into these vectors, conventional methods in the art can be used. Specifically, a DNA is inserted into a vector by the steps of cleaving a genomic DNA containing the objective DNA and a self-replicable vector by restriction enzyme and/or ultrasonication, and ligating the resulting DNA fragment and the resulting vector fragment. The ligation of the DNA fragment and the vector fragment is easily carried out by using type II-restriction enzymes, particularly, such as Sau 3AI, Eco RI, Hin dIII, Bam HI, Sal I, Xba I, Sac I and Pst I. The desired recombinant DNA is obtainable by ligating the both fragment in vivo or in vitro using a DNA ligase, optionally, after annealing them. The recombinant DNA thus obtained is unlimitedly replicable by the steps of introducing into an appropriate host and culturing the resulting transformant.

The recombinant DNA thus obtained can be introduced into an appropriate host-microorganism such as $E.\ coli,\ B.\ subtilis,\ Actinomyces$ and yeasts. The desired transformant can be obtained by applying the colony-hybridization method or by selecting the transformant by the steps of culturing a transformant in nutrient media containing α-1,4 glucan having a glucose polymerization degree of 3 or higher, and selecting a clone which produces ICM from the saccharide.

Any nutrient culture medium can be used for cultivating any microorganism, including a transformant, capable of producing ICM-forming enzyme of the present invention as long as they can grow therein and produce ICM-forming enzyme: For example, synthetic- and natural-culture media can be used as nutrient culture media. Any carbon source can be used as long as it is utilized by the microorganisms: Examples of such carbon source are saccharides such as starch and phytoglycogen, obtainable from plants; glycogen and pullulan, obtainable from animals and microorganisms; hydrolyzates thereof, glucose, fructose, lactose, sucrose, mannitol, sorbitol, and saccharide syrups; and organic acids such as citric acid and succinic acid. The concentrations of these carbon sources in nutrient culture media are appropriately chosen. The nitrogen sources usable in the present invention are, for example, inorganic nitrogen compounds such as ammonium salts and nitrates; organic nitrogen compounds such as urea, corn steep liquor, casein, peptone, yeast extract and beef extract. The inorganic ingredients usable in the invention are, for example, calcium salts, magnesium salts, potassium salts, sodium salts, phosphates, manganese salts, zinc salts, iron salts, copper salts, molybdenium salts, and cobalt salts. If necessary, amino acids and vitamins can be suitably used.

The microorganisms of the present invention are cultured under aerobic conditions, usually, at a temperature in the range of 15-37° C. and at a pH in the range of 5.5-10, preferably, at a temperature in the range of 20-34° C. and at a pH in the range of 5.5-8.5. The cultivation time is set to a time longer than that required for the growth of the microorganisms, preferably, 10-150 hours. The concentration of dissolved oxygen is not specifically restricted, but usually 0.5-20 ppm. The concentration of dissolved oxygen can be kept within the above range by controlling aeration and agitation. The cultivation can be carried out batch-wise or in a continuous manner.

After culturing the microorganisms capable of producing ICM-forming enzyme according to the method described above, the culture containing the enzyme of the present invention is recovered. The major activity of ICM-forming enzyme is found in the cell-free supernatant. Both the cell-free supernatant and the culture can be used as a crude enzyme. Conventional liquid-solid separation methods can be employed to remove cells from the culture. For example, methods to directly centrifuge the resultant culture, as well as those to filtrate the culture with pre-coated filters or to separate cells by membrane filtration using plane filters or follow fibers, can be suitably used. While cell-free supernatants thus obtained can be used intact as a crude enzyme solution, they can be concentrated prior to use. The concentration methods usable in the invention are, for example, salting out using ammonium sulfate, sedimentation using acetone or alcohol, and concentration using membranes such as plane filters and follow fibers.

ICM-forming enzyme can be subjected to conventional immobilization using cell-free supernatants and their concentrates. Examples of such conventional methods are conjugation methods using ion exchangers, covalent bindings and adsorptions using resins and membranes, and inclusion methods using high molecular weight substances.

As described above, a crude enzyme solution can be used intact after concentrating it as ICM-forming enzyme of the present invention. Further, ICM-forming enzyme can be advantageously used after separating or purifying the crude enzyme solution by suitable conventional methods used in the art. For example, a purified ICM-forming enzyme preparation exhibiting an electrophoretically single band can be obtained by salting out a cell-free supernatant with ammonium sulfate, dialyzing the resulting crude enzyme preparation, and successively purifying the dialyzed enzyme preparation on anion-exchange column chromatography using "DEAE-TOYOPEARL 650S", and hydrophobic chromatography using "BUTYL-TOYOPEARL 650M".

In the case of producing ICM-forming enzyme as a recombinant enzyme, the enzyme may be accumulated intracellularly, depending on the kinds of host microorganisms. In such case, while the cell or the culture can be used intact, the recombinant enzyme can be advantageously used after extracting it from cells by using osmotic-shock methods or detergents or by disrupting cells using ultrasonication methods or cell-wall digesting enzymes, and separating it from the cells or cell debris.

Particularly, ICM-forming enzyme of the present invention thus obtained may have the following physicochemical properties:

(1) Molecular Weight
106,000±20,000 daltons when determined on SDS-gel electrophoresis;
(2) Isoelectric Point
pI 7.5±0.5 on isoelectrofocusing Ampholine®, a carrier ampholyte;
(3) Optimum Temperature
50 to 55° C. when reacted at pH 6.0 for 30 min;
(4) Optimum pH
pH 4.5 to 8.0 when reacted at 30° C. for 30 min;
(5) Thermal Stability
Stable up to 35° C. when incubated at pH 6.0 for 60 min
Stable up to 40° C. in the presence of 1 mM $Ca^{2+}$ ion;
(6) pH Stability
Stable in a pH range at 4.5 to 9.0 when incubated at 4° C. for 24 hours; and
(7) N-Terminal Amino Acid Sequence
Having an amino acid sequence of SEQ ID NO:1, i.e., Ala-Ser-Ile-Gly-Thr-Val-Thr-Glu-Asn-Asp-Thr-Ile-Tyr-Gln-Ile-Met-Val-Asp-Arg-Phe.

α-1,4 Glucan having a glucose polymerization degree of 3 or higher, which can be used as a substrate for ICM-forming enzyme of the present invention, includes starch, amylose, amylopectin, glycogen, and their partial hydrolyzates such as amylodextrins, maltodextrins, maltooligosaccharides, obtainable by partially hydrolyzing them with amylases and acids. The partial hydrolyzates obtainable by hydrolyzing starch, amylose, amylopectin, and glycogen by using amylase such as α-amylase (EC 3.2.1.1), maltotetraose-forming amylase (EC 3.2.1.60), and maltohexaose-forming amylase (EC 3.2.1.98), described in "*Handbook of Amylases and Related Enzymes*" published by Pergamon Press Inc., (Tokyo), 1988, can be used as the partial hydrolyzates. Further, starch-debranching enzymes such as pullulanase (EC 3.2.1 41) and isoamylase (EC3.2.1.68) can be arbitrarily used for preparing the partial hydrolyzates.

Both subcelestal starches such as those from corn, wheat, rice, etc., and subterranean starches such as those from potato, sweet potato, tapioca, etc., can be used as substrates. The substrate can be preferably used in the form of a solution prepared by gelatinizing and/or liquefying starch. The ICM content in the reaction mixture is increased with decrease of the degree of partial hydrolysis of starch. Therefore, it is preferable that the DE of the partial starch hydrolyzate is, usually, about 20 or lower, desirably, about 12 or lower, more desirably, about 5 or lower. The ICM content as referred to as in the present specification means the value which is calculated by the following formula:

ICM Content (%)={(Weight of ICM formed)/(Total weight of saccharides in the reaction mixture)}× 100

When ICM-forming enzyme is allowed to act on a substrate, the substrate concentration is not specifically restricted. For example, the reaction by ICM-forming enzyme of the present invention proceeds to form ICM even in the case of using a substrate solution with a relatively low concentration such as 0.1% (w/v). For industrial production, the substrate concentration is preferable to be 1% (w/v) or higher, and ICM can be advantageously produced under the condition. Also, suspensions with a high concentration, containing insoluble substrates, can be used as the substrate solutions. The reaction temperature used in the present enzymatic reaction can be set to a temperature at which the reaction proceeds, i.e. a temperature up to about 60° C., preferably, a temperature in the range of 30 to 50° C. The reaction pH is controlled in the range of, usually, 5 to 9, preferably, 5 to 7. Since the amount of enzyme and the reaction time are closely related, the conditions are adequately chosen with respect to the progress of the objective enzymatic reaction.

ICM of the present invention can be obtained in a high yield, about 20% or higher from starch or its partial hydrolyzate, and about 30% from amylose, by allowing ICM-forming enzyme of the present invention to act on, for example, 1% (w/v) substrate solution containing starch, its partial hydrolyzate, or amylose. The mechanism of ICM-formation by ICM-forming enzyme is estimated as follows:

(1) The enzyme acts on α-1,4 glucan having a glucose polymerization degree of 3 or higher as the substrate and forms various maltooligosaccharides different in glucose polymerization degree by catalyzing intermolecular α-1,4 transglycosylation transferring a series of maltooligosaccharides (disproportionation reaction).

(2) In case of acting on α-1,4 glucan having a glucose polymerization degree of 7 (maltoheptaose), the enzyme hydrolyzes the substrate by a maltopentaose unit and catalyses a cyclization reaction intramolecularly transferring the C-1 position of the reducing end glucose of maltopentaose to the C-6 hydroxyl group of non-reducing end glucose of the same maltopentaose to form $ICG_5$ and maltose.

(3) In case of acting on α-1,4 glucan having glucose polymerization degree of 8 or higher, the enzyme hydrolyzes the substrate by maltopentaose or maltohexaose unit and catalyses a cyclization reaction intramolecularly transferring the C-1 position of the reducing end glucose of maltopentaose or maltohexaose to the C-6 hydroxyl group of non-reducing end glucose of the same maltopentaose or maltohexaose to form $ICG_5$ and $ICG_6$ and α-1,4 glucan whose glucose polymerization degree is reduced by 5 or 6.

(4) The maltose and α-1,4 glucan, newly formed in the above (2) and (3), are converted into ICM by the reactions of (1) to (3) successively.

During the above ICM-forming reactions, other enzymes can be advantageously used in combination with ICM-forming enzyme for increasing ICM content in the reaction mixture. For example, ICM content in the reaction mixture can be advantageously increased by allowing a starch-debranching enzyme such as isoamylase and pullulanase to act on starch in combination with ICM-forming enzyme.

The reaction mixture, thus obtained by the above reaction, can be used intact as a saccharide solution comprising ICM. Optionally, the saccharide solution comprising ICM can be used after hydrolyzing the concomitant oligosaccharides by allowing one or more enzymes selected from the group consisting of α-amylase, β-amylase, glucoamylase, and α-glucosidase to act on the solution. Usually, a saccharide solution comprising ICM is used after purification. Conventional methods used for purifying saccharides can be arbitrarily selected as the purification method. For example, one or more purification methods selected from the group consisting of decoloring with an activated charcoal; desalting with ion exchange resins in H- and OH-form; fractionation by column chromatography such as ion exchange column chromatography, charcoal column chromatography, and silica gel column chromatography; separation using organic solvents such as alcohol and acetone; separation using a membrane having a suitable separability; fermentation using microorganisms, which utilize and decompose concomitant saccharides but not utilize ICM, such as yeasts; and eliminating the remaining reducing sugars with alkaline treatments; can be arbitrarily used.

More particularly, ion exchange column chromatography can be suitably used as an industrial-scale preparation of the objective saccharides. The objective ICM or a saccharide composition comprising the same with an improved purity can be advantageously prepared by, for example, column chromatography using a strongly acidic cation exchange resin as described in Japanese Patent Kokai Nos. 23,799/83 and 72,598/83 to remove concomitant saccharides. In this case, any one of fixed bed, moving bed, and semi-moving bed methods can be employed.

A solution comprising ICM thus obtained or a saccharide solution with an improved ICM content contains ICM in an amount of, usually, 10% (w/w) or higher, desirably, 40% (w/w) or higher, on a dry solid basis, and is usually concentrated into a product in a syrupy form. The syrupy product can be arbitrarily dried to make into a powdery product.

Further, ICM of the present invention have clathrating ability and prevent the volatilization and deterioration of clathrated flavors and effective ingredients. Therefore, ICM can be used for stabilizing and keeping flavors and effective ingredients. In this case, the stabilizing effect by clathrating using ICM can be advantageously enhanced by using ICM together with other cyclic saccharides such as cyclodextrins, branched cyclodextrins, a cyclic tetrasaccharide having a structure of binding four glucose molecules with alternating $\alpha$-1,3 and $\alpha$-1,6 glucosidic linkages, branched cyclic tetrasaccharides, cyclic maltosylmaltose having a structure of binding four glucose molecules with alternating $\alpha$-1,4 and $\alpha$-1,6 glucosidic linkages, cyclodextrans, cyclofructans, etc. The cyclic saccharides such as cyclodextrins are not restricted to products with high purities. For example, a starch hydrolyzate comprising various cyclic saccharides together with a large amount of maltodextrins can be advantageously used as cyclic saccharides with low purities.

In addition, ICM of the present invention are not substantially hydrolyzed by amylase and $\alpha$-glucosidase. Therefore, ICM are not digested and adsorbed when orally taken, and are novel saccharides with no toxicity and no harm.

Thus, ICM and the saccharide compositions comprising the same of the present invention can be advantageously used as a sweetener, taste-improving agent, quality-improving agent, stabilizer, color-deterioration preventing agent, excipient, etc., for various compositions such as foods and beverages, favorite products, feeds, baits, cosmetics, and pharmaceuticals.

ICM of the present invention and the saccharide compositions comprising the same can be used intact as a seasoning for sweetening products. If necessary, they can be advantageously used in combination with other sweeteners, for example, powdery syrup, glucose, isomerized sugar, sucrose, maltose, trehalose, honey, maple sugar, sorbitol, maltitol, dihydrochalcone, stevioside, $\alpha$-glycosyl stevioside, sweetener of Momordica grosvenori, glycyrrhizin, thaumatin, sucralose, L-aspartyl L-phenylalanine methyl ester, saccharine, glycine and alanine; and fillers such as dextrin, starch, and lactose.

Further, powdery products of ICM of the present invention and the saccharide compositions comprising the same can be arbitrarily used intact or, if necessary, after mixing with fillers, excipients, binders, etc., and then shaped into various shapes such as granules, spheres, sticks, plates, cubes, and tablets.

ICM of the present invention and the saccharide compositions comprising the same have sweetness which well harmonizes with other materials having sour-, salty-, astringent-, delicious-, and bitter-taste; and have a high acid- and heat-tolerance. Thus, they can be advantageously used to sweeten and/or improve the taste and quality of general food products.

ICM of the present invention and the saccharide compositions comprising the same can be advantageously used as a sweetener, taste-improving agent, and quality-improving agent for various seasonings such as a soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, ICM and the saccharide compositions comprising the same can be advantageously used to sweeten and to improve the taste and quality of various "wagashi" (Japanese cakes) such as "senbei" (a rice cracker), "arare" (a rice cake cube), "okoshi" (a millet and rice cake), "gyuhi" (a starch paste), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruitpickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of urchin), "ika-no-shiokara" (salted guts of squid), "su-konbu" (processed tangle), "saki-surume" (dried squid strips), "fugu-no-mirin-boshi" (a dried mirin-seasoned swellfish), seasoned fish flour such as of Pacific cod, sea bream, shrimp, etc.; "tsukudani" (foods boiled down in soy sauce) such as those of layer, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, sake, fruit liquor, low-malt beer and beer; soft drinks such as a coffee, cocoa, juice, carbonated beverage, sour milk beverage, and beverage containing a lactic acid bacterium; instant food products such as instant pudding mix, instant hot cake mix, instant juice, instant coffee, "sokuseki-shiruko" (an instant mix of azuki-bean soup with rice cake), and instant soup mix; and other foods and beverages such as solid foods for babies, foods for therapy, drinks, peptide foods, and frozen foods.

ICM and the saccharide compositions comprising the same can be arbitrarily used to improve the taste preference of feeds and pet foods for animals and pets such as domestic animals, poultry, honey bees, silk warms, and fishes; and also they can be advantageously used as a sweetener and taste-improving agent, taste-curing agent, quality-improving agent, and stabilizer for various compositions including favorite products, cosmetics, and pharmaceuticals in a paste or liquid form such as tobacco, cigarette, tooth paste, lipstick, rouge, lip cream, internal liquid medicine, tablet, troche, cod-liver oil in the form of drop, oral refrigerant, cachou, and gargle.

When used as a quality-improving agent or stabilizer, ICM and the saccharide compositions comprising the same can be advantageously used in biologically active substances susceptible to lose their effective ingredients and activities, as well as in health foods, functional foods, and pharmaceuticals containing the biologically active substances. Example of such biologically active substances are liquid preparations containing lymphokines such as α-, β-, and γ-interferons, tumor necrosis factor-α (TNF-α), tumor necrosis factory (TNF-β), macropharge migration inhibitory factor, colony-stimulating factor, transfer factor, and interleukin 2; liquid preparations containing hormones such as insulin, growth hormone, prolactin, erythropoietin, and follicle-stimulating hormone; liquid biological preparations such as BCG vaccine, Japanese encephalitis vaccine, measles vaccine, live polio vaccine, small pox vaccine, tetanus toxoid, Trimeresurus antitoxin, and human immunoglobulin; liquid preparations containing antibiotics such as penicillin, erythromycin, chloramphenicol, tetracycline, streptomycin, and kanamycin sulfate; liquid preparations containing vitamins such as thiamin, riboflavin, L-ascorbic acid, cod liver oil, carotenoid, ergosterol, tocopherol; highly unsaturated fatty acids and their derivatives such as EPA, DHA and arachidonic acid; solution of enzymes such as lipase, esterase, urokinase, protease, β-amylase, isoamylase, glucanase, and lactase; extracts such as ginseng extract, turtle extract, chlorella extract, aloe extract and propolis extract; biologically active substances such as living microorganisms paste of virus, lactic acid bacteria, and yeast, and royal jelly. By using ICM and the saccharide compositions comprising the same, the above biologically active substances can be arbitrary prepared in health foods, functional foods, and pharmaceuticals in a liquid, paste, or solid form, which have a satisfactorily-high stability and quality with less fear of losing or inactivating their effective ingredients and activities.

The methods for incorporating ICM or the saccharide composition comprising the same into the aforesaid compositions are those which can incorporate ICM and the saccharide compositions into the compositions before completion of their processing, and which can be appropriately selected from the following conventional methods; mixing, kneading, dissolving, melting, soaking, penetrating, dispersing, applying, coating, spraying, injecting, crystallizing, and solidifying. The amount of ICM or the saccharide compositions comprising the same to be preferably incorporated into the final compositions is usually in an amount of 0.1% or higher, desirably, 1% or higher.

The following experiments explain the present invention in detail.

Experiment 1

Preparation of Non-Reducing Saccharides

A liquid culture medium consisting of 1.5% (w/v) of "PINE-DEX #4", a partial starch hydrolyzate commercialized by Matsutani Chemical Industries Co., Ltd., Hyogo, Japan, 0.5% (w/v) of "POLYPEPTONE", a yeast extract commercialized by Nihon Pharmaceutical Co., Ltd., Tokyo, Japan, 0.1% (w/v) of "YEAST EXTRACT S", a yeast extract commercialized by Nihon Pharmaceutical Co., Ltd., Tokyo, Japan, 0.1% (w/v) of dipotassium phosphate, 0.06% (w/v) of sodium phosphate dehydrate, 0.05% (w/v) of magnesium sulfate hepta-hydrate, 0.3% (w/v) of calcium carbonate, and water was placed in ten 500 ml-Erlenmeyer flasks in respective amounts of 30 ml, sterilized by autoclaving at 121° C. for 20 min, and cooled. Successively, the culture medium was inoculated with *Bacillus circulans* AM7, FERM BP-10111, and followed by cultivation under rotary-shaking conditions at 27° C. and 230 rpm for 120 hours. After completion of the culture, about 0.3 L of the culture supernatant was obtained by centrifuging the culture broth at 8,000 rpm for 20 minutes to remove cells. 0.25 L of the resulting culture supernatant was used as an enzyme preparation and admixed with 0.25 L of 50 mM acetate buffer (pH 6.0) containing 2% (w/v) of amylose and 2 mM of calcium chloride and followed by the reaction at 40° C. for 48 hours. The reaction was stopped by heating at about 100° C. for 10 min.

Successively, to hydrolyze concomitant reducing saccharides in the reaction mixture into glucose, the above reaction mixture was adjusted to pH 5.0 using hydrochloric acid, then admixed with 400 units/g-dry solid of "TRANSGLUCOSIDASE-L AMANO", α-glucosidase commercialized Amano Enzyme Inc., Aichi, Japan, and 25 units/g-dry solid of glucoamylase commercialized by Nagase ChemteX Corporation, Osaka, Japan, and followed by the reaction at 50° C. for 24 hours. After completion of the reaction, the reaction was stopped by heating at about 100° C. for 10 min. The resulting reaction mixture was subjected to analytical high-performance liquid chromatography (hereinafter, abbreviated as "analytical HPLC") to reveal the saccharides in the mixture. As a result, glucose showing a retention time (Rt) of 57.3 min, a saccharide showing a Rt of 43.3 min (hereinafter, abbreviated as "Saccharide I"), and a saccharide showing a Rt of 37.1 min (hereinafter, abbreviated as "Saccharide II") were detected. The saccharide composition of the mixture is 73.3% of glucose, 24.1% of Saccharide I, and 2.5% of Saccharide II.

Analytical HPLC was carried out under the following conditions:
Column: "MCI gel CK04SS", produced by Mitsubishi Chemical Corporation, Tokyo, Japan; two columns were connected in series
Eluent: Water
Column temperature: 80° C.
Flow rate: 0.4 ml/min
Detector: "RID-10A", a refractive index detector produced by Shimadzu Corporation, Kyoto, Japan.

Figure 2:
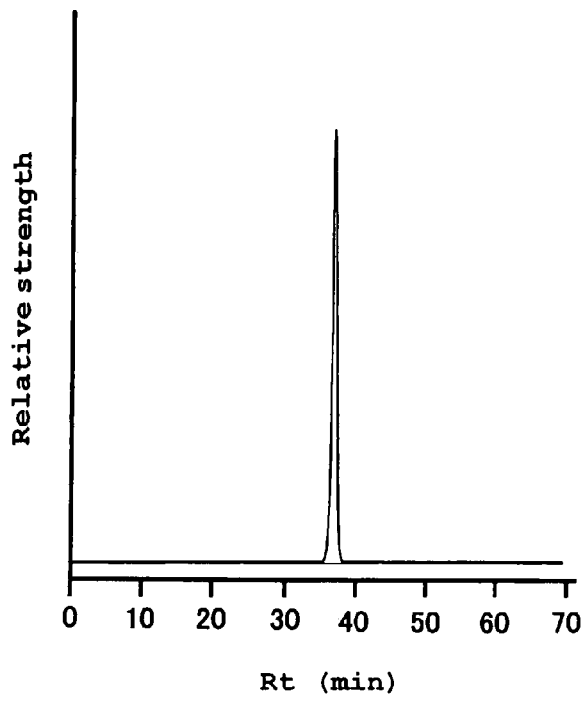
FIG. 2 shows the HPLC elution pattern of the preparation of Saccharide II.

Successively, after removing insoluble substances by filtrating the above reaction mixture, the resulting filtrate was decolored and desalted using "DIAION SK-1B" and "DIAION WA30", ion exchange resins commercialized by Mitsubishi Chemical Corporation, Tokyo, Japan, and "IRA 411", an ion exchange resin commercialized by Organo Corporation, Tokyo, Japan. The resulting solution was concentrated, filtrated, and fractionated by preparative HPLC. As a result, glucose, Saccharide I and Saccharide II were eluted at Rt 29 to 40 min, 57 to 75 min, and 120 to 180 min, respectively. Saccharide I and II were separately collected, filtrated and dried in vacuo. Then, about 850 mg-solid and about 100 mg-solid of Saccharide I and II were obtained. Preparative HPLC was carried out under the following conditions:

Column: "ODS-AQ R-355-15AQ", produced by YMC Corporation, Tokyo, Japan
Eluent: 7.5% (v/v) aqueous methanol solution
Column temperature: 25° C.
Flow rate: 20 ml/min The saccharide compositions of Saccharide I and Saccharide II preparations were analyzed by analytical HPLC, revealing that both contents of Saccharide I and II were respectively 97% or higher as shown in FIGS. 1 and 2. It was revealed that both preparations are highly purified preparations.

The reducing powers of the both saccharide preparations were measured by the Somogyi-Nelson method, revealing that these were less than the measurable limit. It was concluded that Saccharides I and II were substantially non-reducing saccharides.

Experiment 2

Structural Analyses of Saccharide I

Experiment 2-1

Mass Spectrometry

The mass of Saccharide I obtained by the method in Experiment 1 was analyzed using "LCQ Advantage", a mass spectrometer commercialized by Thermo Electron K.K., Kanagawa, Japan. A sodium-added molecular ion with a mass of 833 was remarkably detected and the data revealed that the mass of Saccharide I was 810.

Experiment 2-2

Analysis of Component Sugar

According to conventional method, the component sugar of Saccharide I obtained by the method in Experiment 1 was examined by hydrolyzing the saccharide into monosaccharide with diluted sulfuric acid and analyzing the resulting hydrolyzate by using gas chromatography. As a result, only D-glucose was detected in the hydrolyzate, revealing that Saccharide I was constructed only with D-glucose. Considering the above mass, it was revealed that Saccharide I was a cyclic saccharide composed of five D-glucose molecules.

Experiment 2-3

Methylation Analysis

According to conventional method, Saccharide I obtained by the method in Experiment 1 was subjected to methylation analysis, and the resulting methylation products were analyzed by gas chromatography. The result is in Table 1.

TABLE 1

| Methylation product | Ratio |
| --- | --- |
| 2,3,4-Trimethylated product | 1.00 |
| 2,3,6-Trimethylated product | 3.91 |

As evident from the result in Table 1, 2,3,4-trimethylated product and 2,3,6-trimethylated product were detected in a ratio of about 1:4. Therefore, it was revealed that among five D-glucose molecules constituting Saccharide I, one D-glucose molecule whose hydroxyl groups at the C-1 and C-6 positions were bound with other D-glucose molecule via glucosidic linkages and the other four D-glucose molecules whose hydroxyl groups at their respective C-1 and C-4-positions were bound with other D-glucose molecules via glucosidic linkages.

Experiment 2-4

Nuclear Magnetic Resonance (NMR) Analysis

Figure 3:
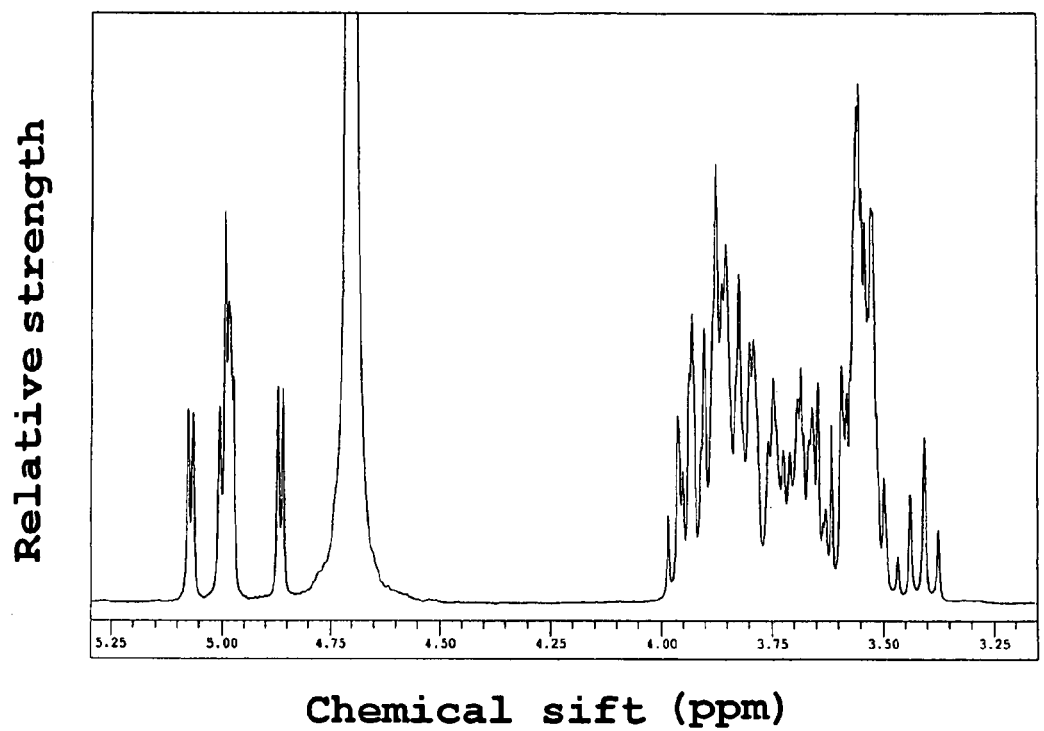
FIG. 3 shows the $^1$H-NMR spectrum of Saccharide I.
Figure 4:
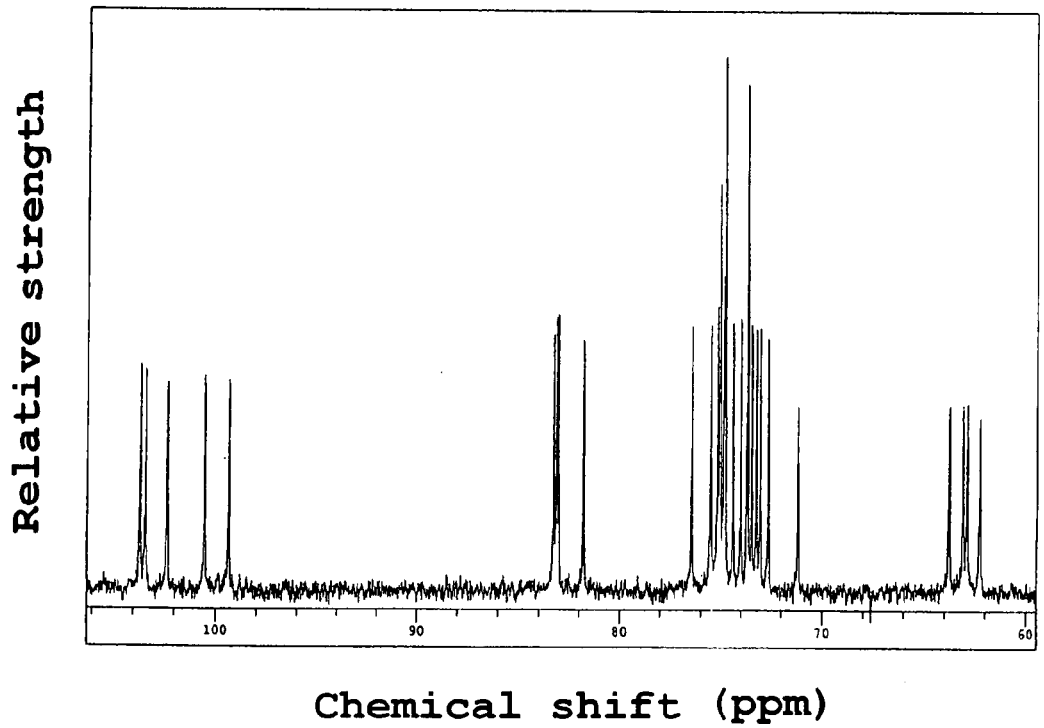
FIG. 4 shows the $^{13}$C-NMR spectrum of Saccharide I.

According to conventional method, Saccharide I obtained by the method in Experiment 1 was subjected to NMR analysis. The $^1$H-NMR and $^{13}$C-NMR spectra are in FIGS. 3 and 4, respectively. Five signals, at about 5.07 ppm, about 5.00 ppm, about 4.99 ppm, about 4.98 ppm, and about 4.87 ppm in $^1$H-NMR spectrum were assigned to proton at the C-1 position of D-glucose residue, and these spin-spin coupling constants were about 3.49 Hz (signal at about 5.07 ppm), about 3.86 Hz (signal at about 5.00 ppm), about 2.39 Hz (signal at about 4.99 ppm), about 2.94 Hz (signal at about 4.98 ppm), and about 3.31 Hz (signal at about 4.87 ppm), respectively. From these results, it was revealed that both anomer types of hydroxyl groups at the C-1 position of D-glucose residue bound via the 1,4-glucosidic and the 1,6-glucosidic linkages were α-type.

Figure 5:
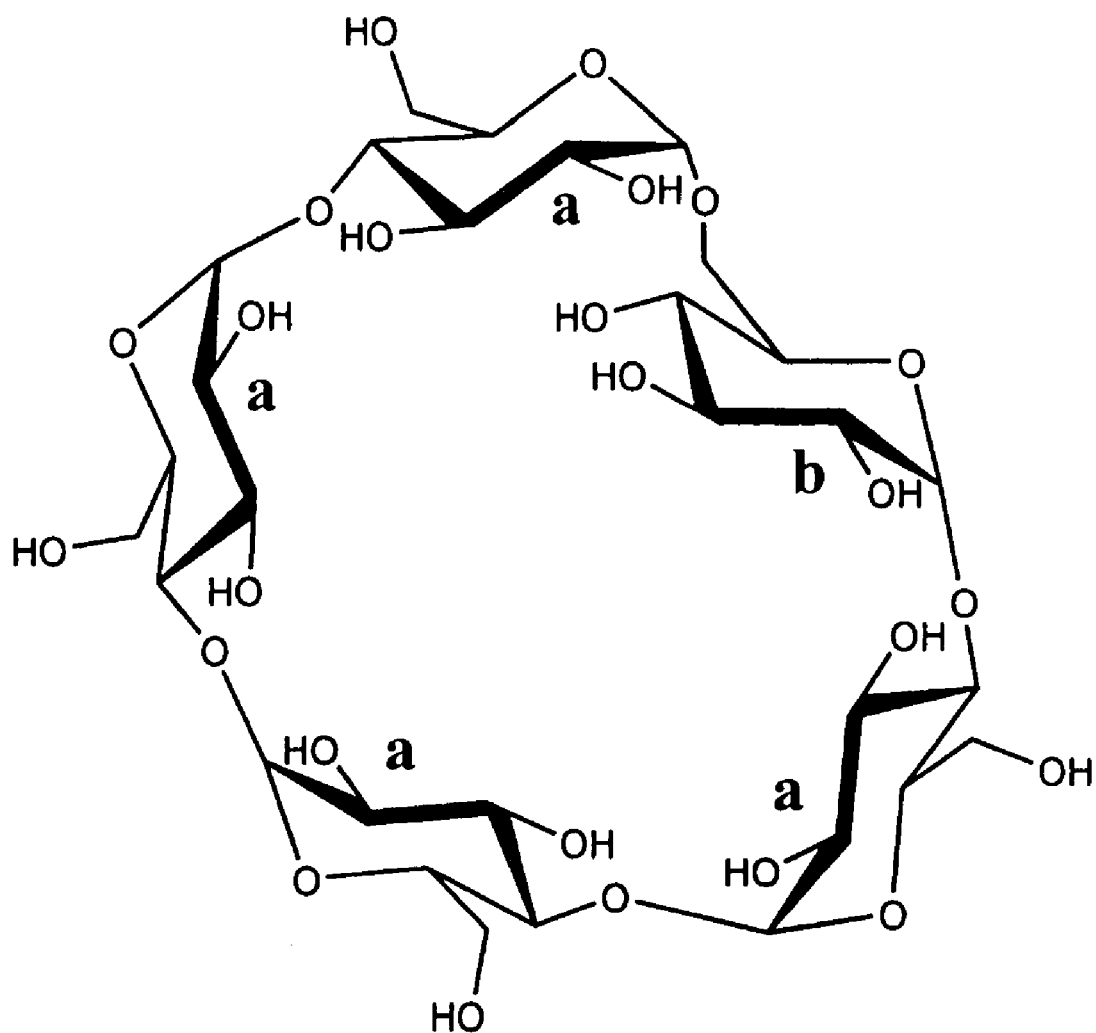
FIG. 5 shows the structure of isocyclomaltopentaose (ICG$_5$) of the present invention.

From the above results, it was revealed that Saccharide I is a cyclic gluco-pentaose having a structure of cyclo{→6)-α-D-glucopyranosyl-(1→4)-α-D-glucopyranosyl-(1→4)-α-D-glucopyranosyl-(1→4)-α-D-glucopyranosyl-(1→4)α-D-glucopyranosyl-(1→} shown in FIG. 5, i.e., isocyclomaltopentaose (ICG$_5$). Since the saccharide, having the above structure, has been unknown before, ICG$_5$ of the present invention is a novel cyclic saccharide.

Experiment 3

Structural Analyses of Saccharide II

Experiment 3-1

Mass Spectrometry

The mass of Saccharide II obtained by the method in Experiment 1 was analyzed using "LCQ Advantage", a mass spectrometer commercialized by Thermo Electron K.K., Kanagawa, Japan. A sodium-added molecular ion with a mass of 995 was remarkably detected and the data revealed that the mass of Saccharide II was 972.

Experiment 3-2

Analysis of Component Sugar

According to conventional method, the component sugar of Saccharide II obtained by the method in Experiment 1 was examined by hydrolyzing the saccharide into monosaccharide with diluted sulfuric acid and analyzing the resulting hydrolyzate by using gas chromatography. As a result, only D-glucose was detected in the hydrolyzate, revealing that Saccharide II was constructed with only D-glucose. Considering the above mass, it was revealed that Saccharide II was a cyclic saccharide composed of six D-glucose molecules.

Experiment 3-3

Methylation Analysis

According to conventional method, Saccharide II obtained by the method in Experiment 1 was subjected to methylation analysis, and the resulting methylation products were analyzed by gas chromatography. The result is in Table 2.

TABLE 2

| Methylation product | Ratio |
| --- | --- |
| 2,3,4-Trimethylated product | 1.00 |
| 2,3,6-Trimethylated product | 4.87 |

As is evident from the result in Table 2, 2,3,4-trimethylated product and 2,3,6-trimethylated product were detected in a ratio of about 1:5. Therefore, it was revealed that among six D-glucose molecules constituting Saccharide II, one D-glucose molecule whose hydroxyl groups at the C-1 and C-6 positions were bound with other D-glucose molecule via glucosidic linkages and five D-glucose molecules whose hydroxyl groups at their respective C-1 and C-4 positions were bound with the other D-glucose molecules via glucosidic linkages.

Experiment 3-4

Nuclear Magnetic Resonance (NMR) Analysis

Figure 6:
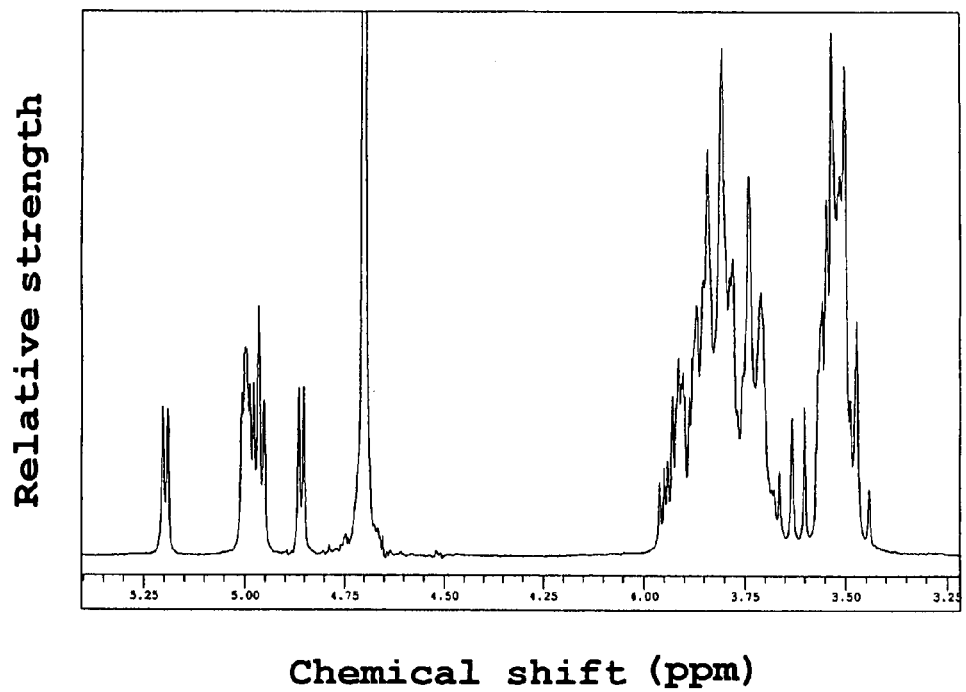
FIG. 6 shows the $^1$H-NMR spectrum of Saccharide II.
Figure 7:
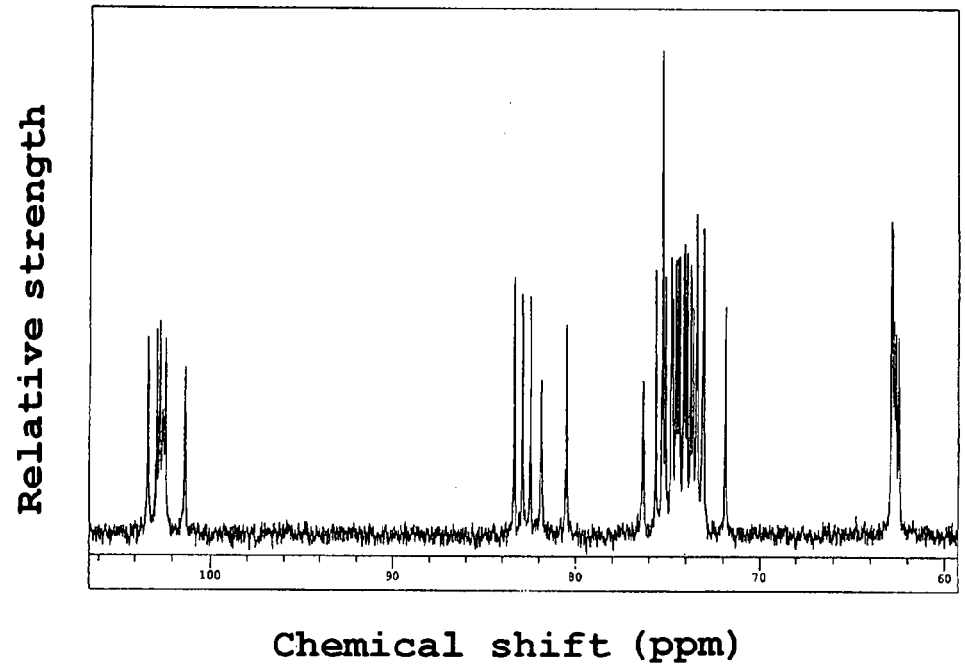
FIG. 7 shows the $^{13}$C-NMR spectrum of Saccharide II.

According to conventional method, Saccharide II obtained by the method in Experiment 1 was subjected to NMR analysis. The $^1$H-NMR and $^{13}$C-NMR spectra are in FIGS. 6 and 7, respectively. Six signals, at about 5.20 ppm, about 5.00 ppm, about 4.99 ppm, about 4.97 ppm, about 4.96 ppm, and about 4.86 ppm, in $^1$H-NMR spectrum were assigned to proton at the C-1 position of D-glucose residue, and these spin-spin coupling constants were about 3.49 Hz (signal at about 5.20 ppm), 2.57 Hz (signal at about 5.00 ppm), 3.13 Hz (signal at about 4.99 ppm), 4.04 Hz (signal at about 4.97 ppm), 3.86 Hz (signal at about 4.96 ppm) and about 3.86 Hz (signal at about 4.86 ppm), respectively. From the results, it was revealed that both anomer types of hydroxyl groups at the C-1 position of D-glucose residue bound via the 1,4-glucosidic and the 1,6-glucosidic linkages were α-type.

Figure 8:
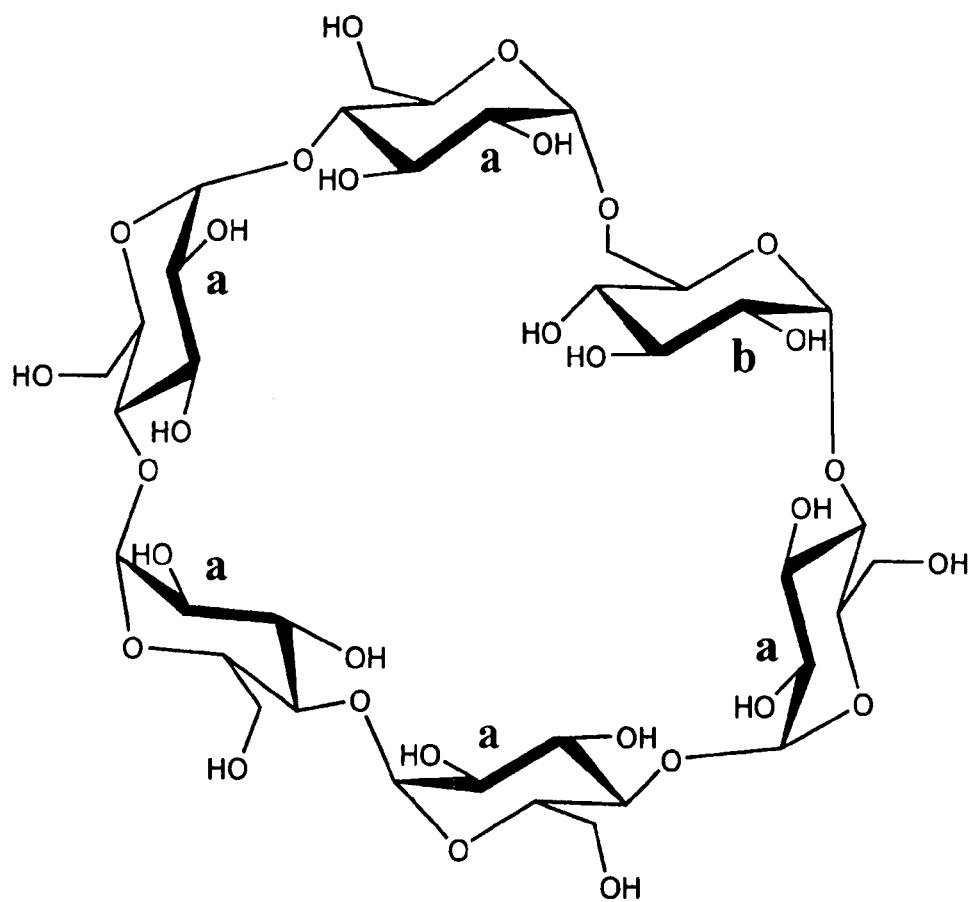
FIG. 8 shows the structure of isocyclomaltohexaose (ICG$_6$) of the present invention.

From the above results, it was revealed that Saccharide II is a cyclic gluco-hexaose having a structure of cyclo{→6)-α-D-glucopyranosyl-(1→4)-α-D-glucopyranosyl-(1→4)-α-D-glucopyranosyl-(1→4)-α-D-glucopyranosyl-(1→4)-α-D-glucopyranosyl-(1→4)-α-D-glucopyranosyl-(1→} shown in FIG. 8, i.e., isocyclomaltohexaose ($ICG_6$). Since the saccharide, having the above structure, has been unknown before, $ICG_6$ of the present invention is a novel cyclic saccharide.

Experiment 4

Preparation of ICM-Forming Enzyme

The liquid culture medium, described in Experiment 1, was placed in two 500 ml-Erlenmeyer flasks in a respective amount of 100 ml, sterilized by autoclaving at 121° C. for 20 min, cooled and inoculated with *Bacillus circulans* AM7, FERM BP-10111, and followed by culturing under rotary-shaking conditions at 27° C. and 230 rpm for 48 hours to prepare a seed culture.

About 20 L of a fresh preparation of the same liquid culture medium as used in the above seed culture were placed in a 30-L fermenter, sterilized by heating, and then cooled to 27° C. and inoculated with about 200 ml of the seed culture, followed by the cultivation at 27° C. and pH 6.0 to 8.0 for 96 hours under aeration-agitation conditions. After completion of the cultivation, the resulting culture broth was distilled from the fermenter and removed cells by centrifuging at 8,000 rpm for 20 min, and about 18 L of culture supernatant was obtained. ICM-forming enzyme activities in the culture broth and culture supernatant were assayed. About 0.027 unit/ml and about 0.025 unit/ml of the enzyme activities were detected in the culture broth and the culture supernatant, respectively. It was revealed that major part of ICM-forming enzyme, produced by *Bacillus circulans* AM7, was secreted extracellularly.

Experiment 5

Purification of ICM-Forming Enzyme

About 10 L (Total activity: about 250 units) of the culture supernatant obtained in Experiment 4 was salted out by adding ammonium sulfate to give finally 80% saturation and allowing it to stand at 4° C. for 24 hours. The resultant precipitates were collected by centrifuging at 11,000 rpm for 30 min, dissolved in 10 mM acetate buffer (pH 6.0), and dialyzed against the same buffer to obtain about 240 ml of a crude enzyme solution. The crude enzyme solution had about 0.96 unit/ml (Total activity: about 230 units) of ICM-forming enzyme. The crude enzyme solution was subjected to anion-exchange column chromatography using 120 ml of "DEAE-TOYOPEARL 650S" gel, an anion-exchange gel commercialized by Tosoh Corporation, Tokyo, Japan. Fraction with ICM-forming enzyme activity was not adsorbed on "DEAE-TOYOPEARL 650S" gel pre-equilibrated with 10 mM acetate buffer (pH 6.0) and when eluted as a non-absorbed fraction. The active fractions were collected and admixed with ammonium sulfate to give a final concentration of 1 M, and then allowed to stand at 4° C. for 24 hours. The enzyme solution was centrifuged to remove precipitates, and subjected to hydrophobic column chromatography using 60 ml of "BUTYL-TOYOPEARL 650M" gel, a gel commercialized by Tosoh Corporation, Tokyo, Japan. ICM-forming enzyme activity was adsorbed on "BUTYL-TOYOPEARL 650M" gel pre-equilibrated with 10 mM acetate buffer (pH 6.0) containing 1 M of ammonium sulfate and when eluted with a linear gradient decreasing from 1 M to 0 M of ammonium sulfate, ICM-forming enzyme activity was eluted at about 0.1 M of ammonium sulfate. The amount of enzyme activity, specific activity and yield of ICM-forming enzyme in each purification step are in Table 3.

TABLE 3

| Purification step | Enzyme* activity (units) | Specific activity of enzyme* (units/mg-protein) | Yield (%) |
|---|---|---|---|
| Culture supernatant | 250 | 0.01 | 100 |
| Dialyzed solution after salting out with ammonium sulfate | 230 | 0.19 | 92 |
| Eluate from ion-exchange column chromatography | 200 | 0.39 | 80 |
| Eluate from hydrophobic column chromatography | 110 | 6.10 | 44 |

*ICM-forming enzyme

The finally purified enzyme preparation of ICM-forming enzyme was assayed for purity on gel electrophoresis using a 5-20% (w/v) gradient polyacrylamide gel and detected on the gel as a single protein band, i.e., a high purity preparation.

Experiment 6

Properties of ICM-Forming Enzyme

Experiment 6-1

Molecular Weight

The purified enzyme preparation of ICM-forming enzyme, obtained by the method in Experiment 5, was subjected to SDS-PAGE (a 5 to 20% (w/v) gradient gel) and molecular weight of ICM-forming enzyme was measured comparing with molecular weight markers, commercialized by Bio-Rad Japan, Tokyo, Japan. It was revealed that ICM-forming enzyme has a molecular weight of 106,000±20,000 daltons.

Experiment 6-2

Isoelectric Point

The purified enzyme preparation of ICM-forming enzyme, obtained by the method in Experiment 5, was subjected to polyacrylamide gel isoelectrofocusing containing 2.2% (w/v) "AMPHOLINE", a carrier ampholyte commercialized by Amersham Biosciences, Tokyo, Japan and isoelectric point of ICM-forming enzyme was measured comparing with isoelectric point markers, commercialized by Amersham Biosciences, Tokyo, Japan. It was revealed that ICM-forming enzyme of the present invention has an isoelectric point (pI) of 7.5±0.5.

Experiment 6-3

Optimum Temperature and pH for the Enzyme Reaction

Figure 9:
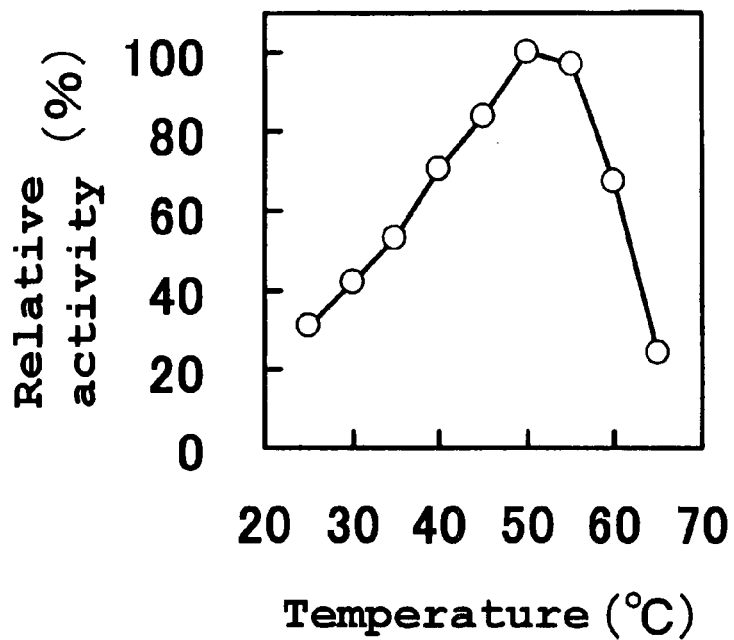
FIG. 9 shows the optimum temperature of ICM-forming enzyme.
Figure 10:
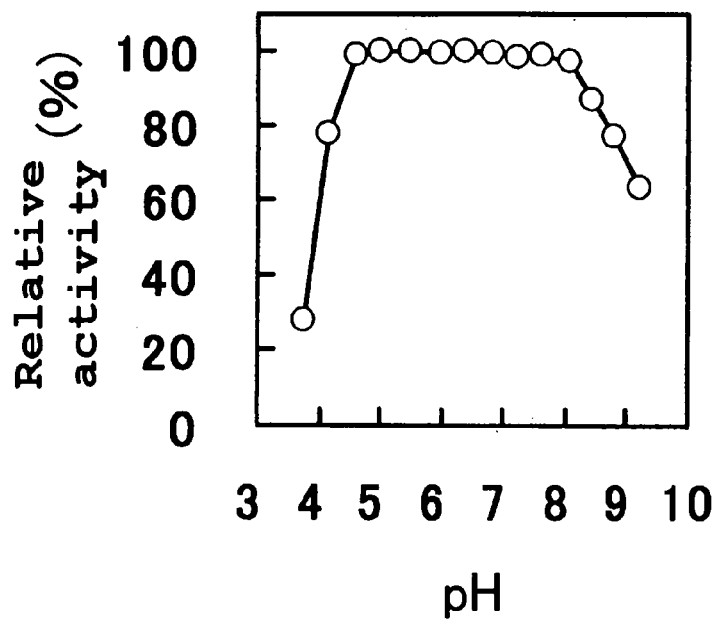
FIG. 10 shows the optimum pH of ICM-forming enzyme.

Effects of temperature and pH on the enzyme activity were investigated using the purified enzyme preparation of ICM-forming enzyme, obtained by the method in Experiment 5, by varying temperature and pH at the assay of the enzyme. The results are in FIG. 9 (Optimum temperature) and FIG. 10 (Optimum pH), respectively. It was revealed that the optimum temperature of ICM-forming enzyme was 50 to 55° C. when reacted at pH 6.0 for 30 min and the optimum pH was 4.5 to 8.0 when reacted at 30° C. for 30 min.

Experiment 6-4

Thermal and pH Stabilities of the Enzyme

Figure 11:
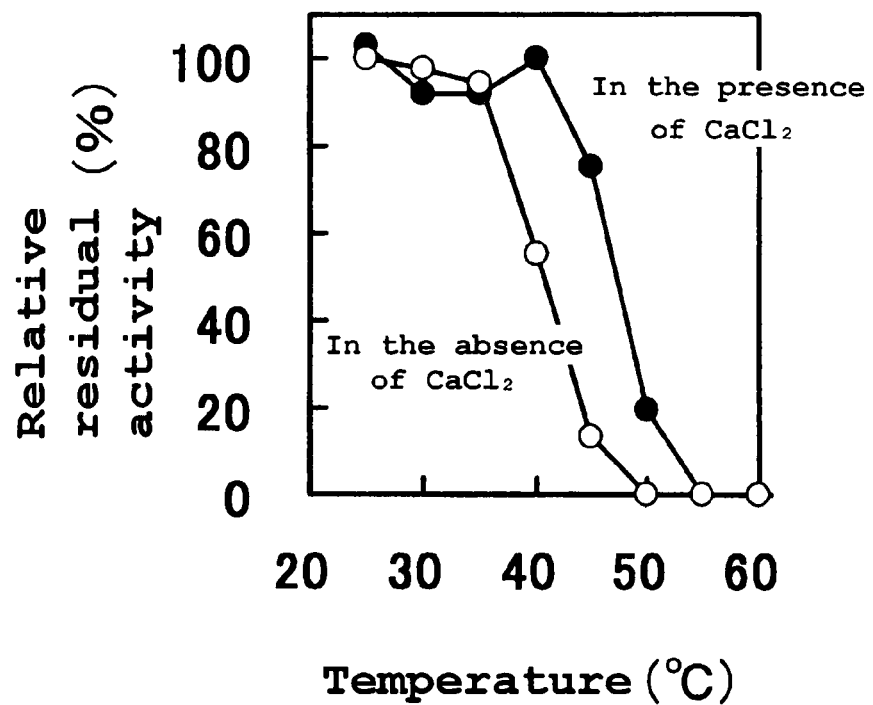
FIG. 11 shows the thermal stability of ICM-forming enzyme.
Figure 12:
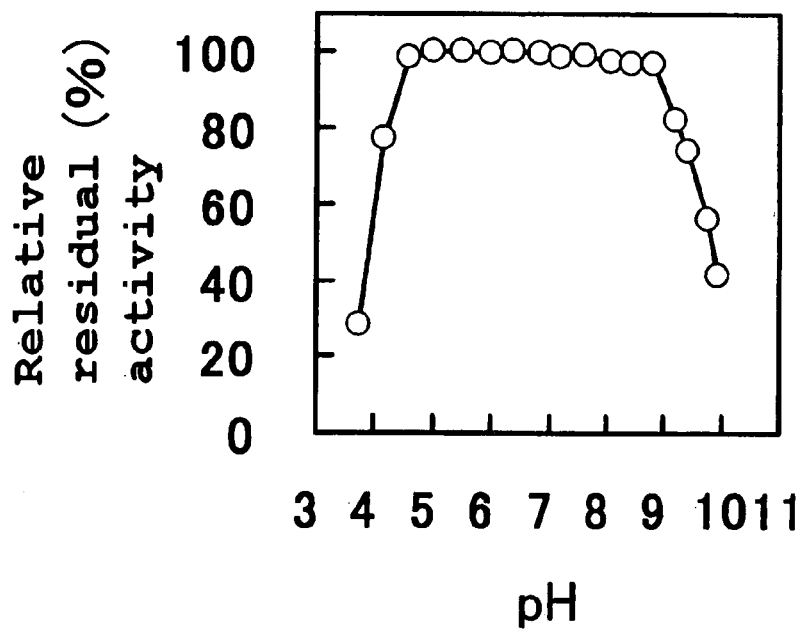
FIG. 12 shows the pH stability of ICM-forming enzyme.

Thermal stability and pH stability of the enzyme were investigated using the purified enzyme preparation of ICM-forming enzyme, obtained by the method in Experiment 5. Thermal stability of the enzyme was determined by the steps of incubating an enzyme solution (10 mM acetate buffer, pH 6.0) under various temperatures for 60 min in the absence or presence of 1 mM $CaCl_2$, cooling in water, and measuring the residual enzyme activity. pH Stability of the enzyme was determined by the steps of incubating enzyme solution in 100 mM buffer at various pHs, and at 4° C. for 24 hours, adjusting the pH to 6.0, and measuring the residual enzyme activity. The results are in FIG. 11 (Thermal stability) and in FIG. 12 (pH Stability), respectively. As is evident from the results in FIG. 11, ICM-forming enzyme is stable up to 35° C. in the absence of $CaCl_2$, and to 40° C. in the presence of 1 mM $CaCl_2$. It was revealed that the thermal stability of the enzyme was improved in the presence of $Ca^{2+}$ ion. As is evident from the results in FIG. 12, it was revealed that ICM-forming enzyme was stable in the range of pH 4.5 to 9.0.

Experiment 6-5

Effects of Metal Ions on the Enzyme Activity

Effects of metal ions on the enzyme activity were investigated using the purified enzyme preparation of ICM-forming enzyme, obtained by the method in Experiment 5, in the presence of 1 mM of respective metal ions according to the assay method. The results are in Table 4.

TABLE 4

| Metal salt | Relative activity (%) | Metal salt | Relative activity (%) |
| --- | --- | --- | --- |
| None | 100 | $NiCl_2$ | 105 |
| $MgCl_2$ | 110 | $CuCl_2$ | 79 |
| $AlCl_3$ | 106 | $ZnCl_2$ | 113 |
| $CaCl_2$ | 105 | $SrCl_2$ | 100 |
| $MnCl_2$ | 108 | $BaCl_2$ | 99 |
| $FeCl_2$ | 94 | $HgCl_2$ | 55 |

TABLE 4-continued

| Metal salt | Relative activity (%) | Metal salt | Relative activity (%) |
| --- | --- | --- | --- |
| $FeCl_3$ | 82 | $PbCl_2$ | 130 |
| $CoCl_2$ | 100 | EDTA | 86 |

As is evident from the results in Table 4, it was revealed that ICM-forming enzyme activity was remarkably inhibited 45% by $HgCl_2$ and about 20% by $FeCl_3$ and $CuCl_2$, respectively. Further, it was revealed that the enzyme activity was also inhibited slightly by EDTA, a chelating agent for metal ions.

Experiment 6-6

N-Terminal Amino Acid Sequence

The N-terminal amino acid sequence of the enzyme was determined using the purified enzyme preparation of ICM-forming enzyme, obtained by the method in Experiment 5, by "Model 429HT", a protein sequencer commercialized by Applied Biosystems Japan, Tokyo, Japan. As a result, it was revealed that the enzyme had the N-terminal amino acid sequence of SEQ ID NO:1, i.e., Ala-Ser-Ile-Gly-Thr-Val-Thr-Glu-Asn-Asp-Thr-Ile-Tyr-Gln-Ile-Met-Val-Asp-Arg-Phe.

Experiment 6-7

Partial Amino Acid Sequences

A part of the purified enzyme preparation of ICM-forming enzyme, obtained by the method in Experiment 5, was dialyzed against 10 mM Tris-HCl buffer (pH 9.0) at 4° C. for 18 hours, and the dialyzed solution was diluted with a fresh preparation of the same buffer to give a concentration of about one mg-protein/ml. About one milliliter of the diluted solution was admixed with 20 μg of "LYSYL ENDOPEPTIDASE" commercialized by Wako Pure Chemicals, Ltd, Tokyo, Japan, and incubated at 30° C. for 20 hours to hydrolyze the enzyme protein. The resulting hydrolyzate was injected to "μ-BONDASPHERE C18 column", having a diameter of 3.9 mm and a length of 150 mm, a HPLC column commercialized by Waters Chromatography Div., MILLIPORE Corp., Milford, USA, pre-equilibrated with 0.1% (v/v) trifluoroacetate, and peptides were fractionated at a flow rate of 0.9 ml/min and at ambient temperature, using a linear gradient of acetonitrile increasing from 10% (v/v) to 50% (v/v) in 0.1% (v/v) trifluoroacetate over 100 min. Peptide fragments eluted from the column were detected by monitoring the absorbance at a wavelength of 210 nm. Nine kinds of peptide fragments eluted at retention times of about 14 min, about 18 min, about 30 min, about 35 min, about 38 min, about 61 min, about 64 min, about 67 min, and about 82 min were separately collected, and their amino acid sequences were analyzed according to the method in Experiment 6-6. These peptide fragments had amino acid sequences of SEQ ID NO:4 to 12.

Experiment 7

Cloning of a DNA Encoding ICM-Forming Enzyme and Preparation of a Recombinant DNA Comprising the DNA and a Transformant A DNA encoding ICM-forming enzyme was cloned from *Bacillus circulans* AM7 (FERM BP-10111), and a self-replicable recombinant DNA containing the DNA was constructed. Successively, the nucleotide sequence of the DNA encoding the enzyme was determined and a transformant was also prepared.

Experiment 7-1

Preparation of Chromosomal DNA

A liquid culture medium consisting of 0.25% (w/v) of "PINE-DEX #4", a partial starch hydrolyzate commercialized by Matsutani Chemical Industries Co., Ltd., Hyogo, Japan, 0.2% (w/v) of "FUNMATSU-KOBO-EKISU S", a yeast extract commercialized by Nihon Pharmaceutical Co., Ltd., Tokyo, Japan, 1.0% (w/v) of "POLYPEPTONE", a yeast extract commercialized by Nihon Pharmaceutical Co., Ltd., Tokyo, Japan, 0.1% (w/v) of dipotassium phosphate, 0.06% (w/v) of sodium phosphate dihydrate, 0.05% (w/v) of magnesium sulfate hepta-hydrate, 0.1% (w/v) of calcium carbonate and water was placed in 500 ml-Erlenmeyer flasks in respective amounts of 100 ml, sterilized by autoclaving at 121° C. for 20 min, cooled and inoculated with *Bacillus circulans* AM7, FERM BP-10111, followed by the cultivation under rotary-shaking conditions at 27° C. and 230 rpm for 5 days.

The cells collected from the culture by centrifugation were suspended in TES buffer (pH 8.0), then the suspension was admixed with lysozyme to give a concentration of 0.05% (w/v), and incubated at 37° C. for 30 min. After freezing the resulting lysate at −80° C. for one hour, the lysate was admixed with TSS buffer (pH 9.0) and heated to 60° C. The solution was admixed with a mixture of TES buffer and phenol, and was vigorously shaken for 10 min with cooling in an ice bath, and the supernatant was collected by centrifugation. The supernatant was admixed with twice volume of cold ethanol, and the resulting precipitate was collected as a crude chromosomal DNA. The crude chromosomal DNA was dissolved in SSC buffer (pH 7.1), admixed with 7.5 µg of ribonuclease and 125 µg of proteinase, and incubated at 37° C. for one hour. The chromosomal DNA was extracted from the reaction mixture by adding chloroform/isoamylalcohol mixture, then, admixed with cold ethanol, and the resulting precipitate containing chromosomal DNA was collected. The purified chromosomal DNA, obtained according to the method described above, was dissolved in SSC buffer (pH 7.1) to give a concentration of about one mg/ml and frozen at −80° C.

Experiment 7-2

PCR Cloning of a Partial DNA Fragment

Before cloning a DNA encoding ICM-forming enzyme, a partial DNA fragment was cloned by PCR-cloning method. Two kinds of sense primers, F1 and F2, having the nucleotide sequences of SEQ ID NOs:13 and 14, were synthesized based on the 10th to 15th and the 13th to 18th amino acid sequences in SEQ ID NO:1, the N-terminal amino acid sequence of ICM-forming enzyme, respectively. While, two kinds of antisense primers, R1 and R2, having the nucleotide sequences of SEQ ID NOs:15 and 16, were synthesized based on the 4th to 8th and the 1st to 5th amino acid sequences in SEQ ID NO: 4, an internal amino acid sequence of the enzyme, respectively. By using the sense primer F1 and the antisense primer R1, 1st PCR was carried out using the chromosomal DNA obtained in Experiment 7-1 as a template according to conventional method. Successively, by using the sense primer F2 and antisense primer R2, 2nd PCR was carried out by using the 1st PCR products as templates. As a result, two kinds of PCR-amplified DNA fragments with about 200 bp and about 300 bp were obtained. The PCR-amplified DNA fragments were inserted to Srf I site of "pCR-Script Amp SK(+)", a plasmid commercialized by Stratagene and then used for transforming "Epicurian Coli XL2-Blue", a competent cell commercialized by Stratagene Cloning System, by conventional competent cell method. Recombinant DNAs were extracted from the resulting transformants by conventional alkaline-SDS method and a transformant introduced with a recombinant DNA inserted with the about 300 bp DNA fragment was selected. Successively, the nucleotide sequence of the recombinant DNA was analyzed by conventional dideoxy method, revealing that the recombinant DNA contains a DNA fragment having a 251 bp-nucleotide sequence of SEQ ID NO:17.

Amino acid sequences of 37th to 46th and 47th to 60th in the amino acid sequence shown in parallel with the nucleotide sequence of SEQ ID NO:17 were completely identical with the amino acid sequences of SEQ ID NOs: 6 and 10, which are partial amino acid sequences of ICM-forming enzyme. From the results, it was revealed that the above DNA fragment is one encoding a part of ICM-forming enzyme originated from *Bacillus circulans* AM7 (FERM BP-10111).

Experiment 7-3

Cloning of a DNA Encoding ICM-Forming Enzyme by Colony Hybridization Method

One tenth milliliter of a purified chromosomal DNA solution, prepared in Experiment 7-1, was admixed with about 100 units of a restriction enzyme, Hin dIII, and incubated at 37° C. for one hour to digest the chromosomal DNA. The resulting DNA fragments corresponding to about 5,000 to 9,000 bp were collected by agarose gel electrophoresis. A plasmid vector, "Bluescript II SK(+)®", commercialized by Stratagene Cloning System, was completely digested with a restriction enzyme, Hin dIII by conventional method. A recombinant DNA was obtained by ligating 0.5 µg of the digested plasmid vector with about 5 µg of the DNA fragments using a "DNA Ligation Kit", commercialized by Takara Shuzo Co., Ltd., according to the method described in a specification attached with the kit. Then, a Hin dIII-gene library was prepared by transforming the competent cell, "Epicurian Coli XL2-BLUE", commercialized by Stratagene Cloning System, with the recombinant DNA by conventional competent cell method.

The transformants thus obtained as gene library were inoculated into a fresh agar plate medium (pH 7.0) containing 10 g/L of tryptone, 5 g/L of yeast extract, 5 g/L of sodium chloride, 100 mg/L of ampicillin sodium salt, and 50 mg/L of 5-bromo-4-chloro-3-indolyl-β-galactoside, and incubated at 37° C. for 24 hours. About 655 white colonies grown on the plate were transferred to and fixed on a nylon membrane, "Hybond-N+", commercialized by Amasham Bioscience K.K. The recombinant DNA prepared in Experiment 7-2 was digested by restriction enzymes, Not I and Bam HI, and the objective DNA fragment of about 300 bp was collected by conventional agarose gel electrophoresis. The resulting DNA fragment was labeled using "DIG DNA Labeling and Detection Kit", a DNA-labeling kit commercialized by Roche Diagnostics K. K., Tokyo, Japan, to make into a DIG(digoxigenin)-labeled probe. Conventional colony hybridization was carried out on the aforesaid 655 colonies fixed on nylon membrane using the DIG-labeled probe, and a transformant was obtained as a positive clone. The transformant was named "BAMH1".

Experiment 7-4

Determination of a Nucleotide Sequence of a DNA Encoding ICM-Forming Enzyme

Figure 13:
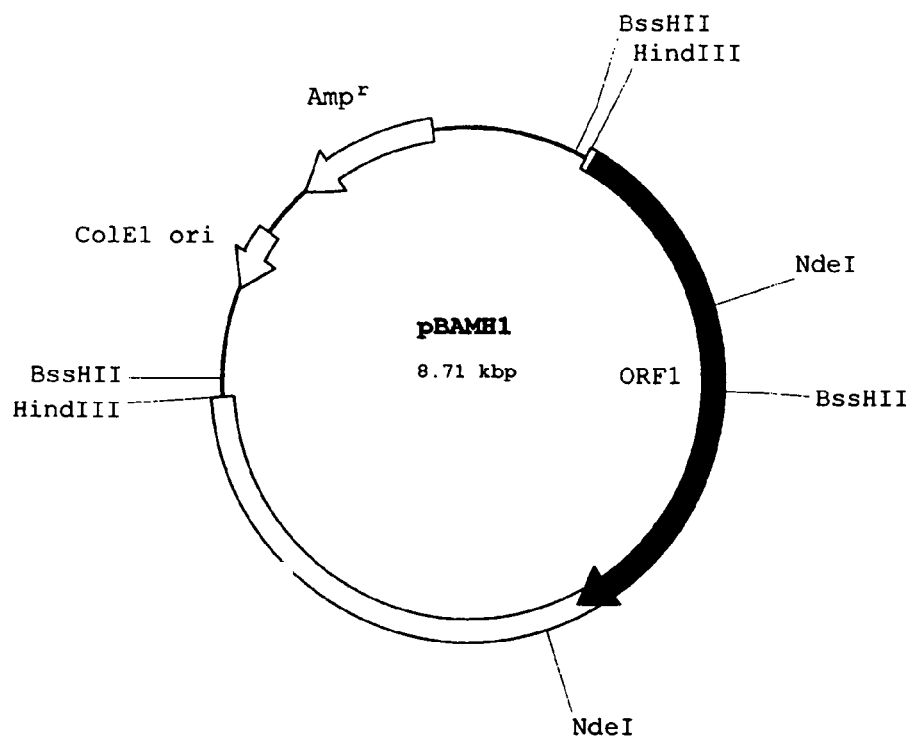
FIG. 13 shows a recombinant DNA, pBAMH1, of the present invention.

According to conventional method, the transformant, BAMH1 was inoculated into L-broth medium (pH7.0) containing 100 µg/ml of ampicillin sodium salt, and cultured under rotary-shaking conditions at 37° C. for 24 hours. After completion of the culture, cells were collected by centrifugation from the culture, and the recombinant DNA was extracted from the cells by conventional alkaline-SDS method. Analysis of the nucleotide sequence of the recombinant DNA using conventional dideoxy method revealed that the recombinant DNA contained a DNA having the nucleotide sequence of SEQ ID NO:18, 2,985 bp, which originated from *Bacillus circulans* AM7 (FERM BP-10111). As shown in FIG. 13, in the recombinant DNA, the DNA was ligated at the downstream of recognition site of a restriction enzyme, Hin dIII. The amino acid sequence deduced from the nucleotide sequence is as shown in parallel in SEQ ID NO:18. The amino acid sequence was compared with those of ICM-forming enzyme of the present invention, i.e., the N-terminal amino acid sequence of SEQ ID NO:1 determined by the method in Experiment 6-6 and the internal partial amino acid sequences of SEQ ID NO:4 to 12 determined by the method in Experiment 6-7. An amino acid sequence of SEQ ID NO:1 was completely identical with that of 36th to 55th of the amino acid sequence shown in parallel in SEQ ID NO: 18. Amino acid sequences of SEQ ID NO: 4, 5, 6, 7, 8, 9, 10, 11, and 12 were completely identical with those of 126th to 135th, 140th to 149th, 84th to 93rd, 152nd to 163rd, 806th to 816th, 925th to 939th, 94th to 107th, 185th to 197th, and 272nd to 286th of the amino acid sequence shown in parallel in SEQ ID NO:18, respectively. These results indicate that ICM-forming enzyme of the present invention contains the amino acid sequence of SEQ ID NO:2, and that the enzyme is encoded by the DNA having the nucleotide sequence of SEQ ID NO:3 in the case of *Bacillus circulans* AM7 (FERM BP-10111). An amino acid sequence of the 1st to 35th of that shown in parallel in SEQ ID NO:18 was estimated to be a secretion signal sequence of the enzyme. According to the results described above, it was revealed that the precursor of the enzyme before secretion had the amino acid sequence shown in parallel in SEQ ID NO:18, and the amino acid sequence was encoded by the nucleotide sequence of SEQ ID NO:18. The recombinant DNA, prepared and confirmed its nucleotide sequence as described above, was named "pBAMH1".

Experiment 8

Preparation of a Recombinant DNA for Expression, pETAM1 and Production of a Recombinant ICM-Forming Enzyme by its Transformant, ETAM1

The gene encoding ICM-forming enzyme in the recombinant DNA, pBAMH1, was inserted to an expression vector, and the expression of a recombinant ICM-forming enzyme in *E. coli* was investigated.

Experiment 8-1

Preparation of a Recombinant DNA for Expression, pETAM1 and a Transformant, ETAM1

When the gene encoding ICM-forming enzyme in pBAMH1 was inserted to an expression vector, PCR-mutations were introduced to the gene for the purpose of introducing a Nde I recognition site to the upstream of the structural gene of ICM-forming enzyme and deleting a Nde I recognition site which presents in the structural gene. Using pBAMH1 as a template, 1st PCR was carried out to obtain an amplified DNA fragment using two sense primers and two antisense primers by the following combinations:

Combination 1

A sense primer having a nucleotide sequence of SEQ ID NO:19, synthesized based on a nucleotide sequence of pBluescript II SK(+), the vector of pBAMH1, which was located at the upstream of the structural gene of ICM-forming enzyme; and an antisense primer having a nucleotide sequence of SEQ ID NO:22, synthesized based on a nucleotide sequence of a Nde I site presented in the structural gene encoding ICM-forming enzyme.

Combination 2

A sense primer having a nucleotide sequence of SEQ ID NO:21, synthesized based on a nucleotide sequence of a Nde I site presented in the structural gene encoding ICM-forming enzyme; and an antisense primer having a nucleotide sequence of SEQ ID NO:23, synthesized based on a nucleotide sequence of Bam HI site, which was located at the downstream of the structural gene of ICM-forming enzyme.

Figure 14:
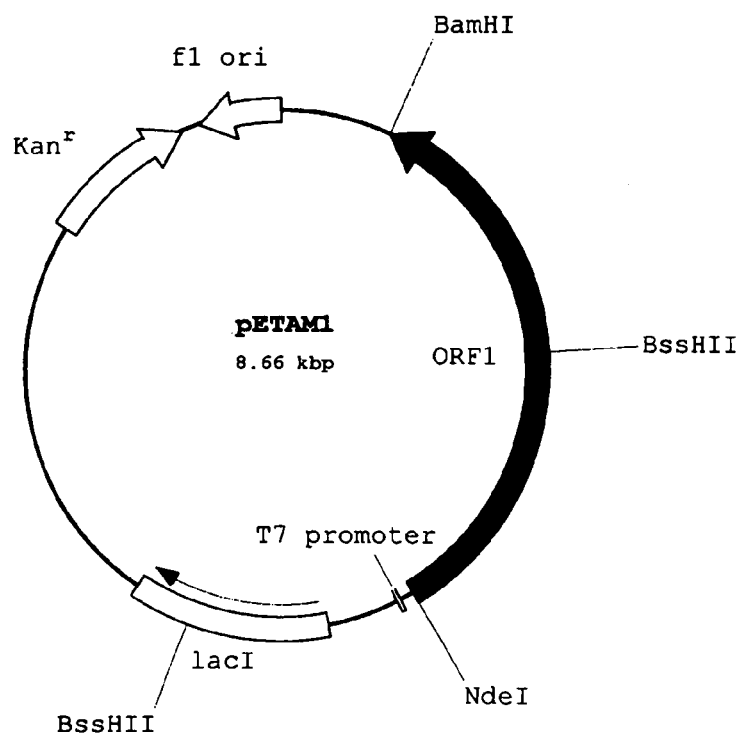
FIG. 14 shows a recombinant DNA, pETAM1.

Successively, using the resulting amplified DNA fragment as a template, 2nd PCR was carried out using a sense primer having a nucleotide sequence of SEQ ID NO:20, which was synthesized for introducing a Nde I site to the upstream of the structural gene; and an antisense primer having a nucleotide sequence of SEQ ID NO:23, synthesized based on a nucleotide sequence of Bam HI site located at the downstream of the structural gene; in combination to amplify the objective gene encoding ICM-forming enzyme which introduced a Nde I site to the upstream of the structural gene and deleted a Nde I site in the structural gene. A recombinant DNA was constructed by inserting the above amplified DNA to a vector prepared by digesting "pET-38b(+)", an expression vector commercialized by Novagen, with restriction enzymes, Nde I and Bam HI, and named "pETAM1".

pETAM1 was shown in FIG. 14. *E. coli* JM109, commercialized by TOYOBO Co., Ltd., Tokyo, Japan, was transformed by using pETAM1 and then pETAM1 was prepared from the resulting transformant. A transformant, "ETAM1", was prepared by transforming *E. coli* BL21 (DE), a host for gene expression, commercialized by Novagen, using pETAM1.

Experiment 8-2

Production of a Recombinant ICM-Forming Enzyme by a Transformant, ETAM1

A liquid culture medium consisting of 10 g/L of "BACT-TRYPTONE", tryptone commercialized by Difco Laboratories, 5 g/L of "BACTO-YEAST EXTRACT", a yeast extract commercialized by Difco Laboratories, 10 g/L of sodium chloride, and water was placed in a 500 ml-Erlenmeyer flask in respective amount of 100 ml, sterilized by autoclaving at 121° C. for 20 min, and cooled. Then, the liquid medium was prepared by sterilely adjusting to pH 7.0 and admixing with 2 mg of kanamycin. A transformant, ETAM1, obtained by the method in Experiment 8-1, was inoculated into the above liquid medium, and cultured at 27° C. under a rotary-shaking condition. The cultivation was continued until the turbidity of culture reached about 0.6, and then admixed with isopropyl-1-thio-β-D-galactopyranoside (IPTG) to give a final concentration of 0.4 mM for inducing the expression of a gene encoding ICM-forming enzyme, and the cultivation was further continued for three hours. Cells and supernatant were separately collected from the culture by conventional centrifugation. In the case of the cells, whole-cell extract was prepared by ultrasonic disruption. The ultrasonic disruption was carried out by suspending cells in 20 mM Tris-HCl buffer (pH 7.5) and disrupting cells in suspension in an ice bath using a ultrasonic homogenizer, "Model UH-600", commercialized by MST Corporation, Aichi, Japan, and the resulting homogenate was used as a whole-cell extract.

ICM-Forming enzyme activities of the culture supernatant and whole-cell extract, prepared as described above, were assayed, and those values were expressed in terms of the activities/ml-culture, respectively. As a control, ICM-forming enzyme activities of the culture supernatant and the whole-cell extract of *E. coli* BL21(DE3), a host, having a plasmid, pET-38b(+), were assayed after culturing the host and preparing the culture supernatant and the whole-cell extract in the same manner. The results are in Table 5.

TABLE 5

| Strain | ICM-forming enzyme activity (units/ml-broth) | |
|---|---|---|
| | Culture supernatant | Whole cell extract |
| ETAM1 (The present invention) | 0.00 | 0.12 |
| *E. coli* BL21 (DE3) pET-38b(+)(Control) | 0.00 | 0.00 |

As is evident from the results in Table 5, it was revealed that the transformant, ETAM1 produced ICM-forming enzyme of the present invention intracellularly. In the case of the host, *E. coli* BL21 (DE3), no enzyme activity was detected in both of the culture supernatant and the whole-cell extract.

The whole-cell extract, obtained by the method in Experiment 8, was further purified by salting out, dialysis and successive column chromatographies on "DEAE-TOYOPEARL 650S" gel and "BUTYL-TOYOPEARL 650M" gel according to the methods in Experiment 5, and the purified enzyme preparation was analyzed according to the methods in Experiment 6. As a result, the molecular weight was about 106,000±20,000 daltons by SDS-polyacrylamide gel electrophoresis; the isoelectric point was about 7.5±0.5 by polyacrylamide gel isoelectrofocusing; the optimum temperature of ICM-forming enzyme activity was about 50 to 55° C. when reacted at pH 6.0 for 30 min; the optimum pH of the enzyme was about 4.5 to 8.0 when reacted at 30° C. for 30 min; the thermal stability was up to 35° C. in the absence of $CaCl_2$ and up to about 40° C. in the presence of 1 mM $CaCl_2$ when incubated at various temperatures for 60 min; and the pH stability was in the range of about pH 4.5 to about 9.0 when incubated at various pHs at 4° C. for 24 hours. These physicochemical properties were substantially identical to those of the enzyme prepared by the method in Experiment 5. The results described above indicate that ICM-forming enzyme of the present invention can be advantageously produced by recombinant DNA technique.

Experiment 9

Action on Various Saccharides

Substrate specificity of ICM-forming enzyme was investigated using various saccharides as substrates. Substrate solutions were prepared by dissolving maltose, maltotriose, maltotetraose, maltopentaose, maltohexaose, maltoheptaose, neotrehalose, trehalose, kojibiose, nigerose, isomaltose, isomaltotriose, panose, isopanose, maltitol, maltotriitol, α-, β-, or γ-cyclodextrin, amylose, soluble starch, glycogen, pullulan or dextran in water. Each substrate solution was admixed with acetate buffer (pH 6.0) and $CaCl_2$ to give final concentrations of 20 mM and 1 mM, respectively. Then, each of the resulting substrate solutions was further admixed with one unit/g-substrate, on a dry solid basis, of the purified preparation of ICM-forming enzyme, obtained by the method in Experiment 5. Substrate concentration was set to 2% (w/v) and followed by the enzyme reaction at 40° C. and pH 6.0 for 24 hours. To examine the saccharides in each mixture before and after the reaction, saccharides were separated by silica gel thin-layer chromatography (hereinafter, simply abbreviated as "TLC") using "KIESELGEL 60", a TLC aluminum plate (10×20 cm) and a solvent (n-butanol/pyridine/water, volume ratio of 6:4:1) and two-times ascending method. The separated saccharides on the plate were detected by visualizing the spots with sulfate-methanol method. By the above TLC analyses, the enzymatic action and the degree of the reaction of ICM-forming enzyme on each substrate were confirmed. The results are in Table 6.

TABLE 6

| Substrate | Action* | Substrate | Action* |
|---|---|---|---|
| Maltose | – | Panose | – |
| Maltotriose | + | Isopanose | – |
| Maltotetraose | ++ | Maltitol | – |
| Maltopentaose | +++ | Maltotriitol | – |
| Maltohexaose | +++ | α-Cyclodextrin | – |
| Maltoheptaose | +++ | β-Cyclodextrin | – |
| Neotrehalose | – | γ-Cyclodextrin | – |
| Trehalose | – | Amylose | +++ |
| Kojibiose | – | Soluble starch | ++ |
| Nigerose | – | Glycogen | + |
| Isomaltose | – | Pullulan | – |
| Isomaltotriose | – | Dextran | – |

*In comparison with before and after the reaction, the symbol, "–" means "Not changed". The symbol, "+" means "Spot of substrate is slightly decreased and the formation of ICM are detected". The symbol, "++" means "Spot of substrate is markedly decreased and the formation of ICM are detected". The symbol, "+++" means "Spot of substrate is virtually disappeared and the formation of ICM are detected".

As is evident from the results in Table 6, ICM-forming enzyme acts on maltotetraose, maltopentaose, maltohexaose, and maltoheptaose, and slightly on maltotriose among the saccharides tested. Further, ICM-forming enzyme of the present invention acts on amylose, starch, and glycogen. From the results, it was revealed that the enzyme acts on α-1,4 glucans having a glucose polymerization degree of 3 or higher.

Experiment 10

Action Mechanism

Experiment 10-1

Product from Maltohexaose by the Enzyme Reaction

A substrate solution was prepared by mixing maltohexaose solution, acetate buffer (pH 6.0) and $CaCl_2$ to give final concentrations of 1% (w/v), 20 mM, and 1 mM, respectively. The substrate solution was admixed with one unit/g-substrate, on a dry solid basis, of ICM-forming enzyme, obtained by the method in Experiment 5, and followed by the enzyme reaction at 45° C. and pH 6.0. Aliquots were sampled from the reaction mixture with time and the reaction was stopped by keeping at 100° C. for 10 min. Saccharide compositions of the samples were measured by HPLC. HPLC was carried out under the following conditions:

Column: "MCI gel CK04SS", produced by Mitsubishi Chemical Corporation, Tokyo, Japan; two columns were connected in series Eluent: Water Column temperature: 80° C.

Flow rate: 0.4 ml/min

Detector: "RID-10A", a refractive index detector produced by Shimadzu Corporation, Kyoto, Japan.

The results are in Table 7.

TABLE 7

| Saccharide | Saccharide composition (%) | | | |
|---|---|---|---|---|
| | Before the reaction | 1 hour | 2 hours | 4 hours |
| Glucose | 0.0 | 0.0 | 0.0 | 0.0 |
| Maltose | 0.0 | 3.4 | 4.7 | 6.1 |
| Maltotriose | 0.0 | 7.0 | 8.6 | 9.7 |
| Maltotetraose | 0.0 | 5.8 | 7.5 | 8.8 |
| Maltopentaose | 1.7 | 8.1 | 9.6 | 10.6 |
| Isocyclomaltopentaose | 0.0 | 5.5 | 8.0 | 10.8 |
| Maltohexaose | 97.5 | 41.7 | 29.1 | 19.2 |
| Isocyclomaltohexaose | 0.0 | 0.4 | 0.5 | 0.7 |
| Maltoheptaose | 0.8 | 4.4 | 5.2 | 6.0 |
| Maltooctaose | 0.0 | 3.4 | 4.4 | 5.2 |
| Maltononaose | 0.0 | 4.8 | 4.6 | 4.5 |
| Maltodecaose | 0.0 | 2.8 | 3.3 | 3.6 |
| Maltoundecaose | 0.0 | 7.3 | 6.9 | 5.7 |
| Others | 0.0 | 5.4 | 7.6 | 9.1 |

As is evident from the results in Table 7, it was revealed that ICM-forming enzyme forms from maltohexaose maltooligosaccharides having glucose polymerization degrees of lower than that of maltohexaose, $ICG_5$, $ICG_6$, and maltooligosaccharides having glucose polymerizations degrees of higher than that of maltohexaose. The results suggested that ICM-forming enzyme of the present invention acts on maltohexaose and catalyzes "disproportionation" reaction, forming a series of maltooligosaccharides different in glucose polymerization degree, including maltooligosaccharides having a glucose polymerization degree of 2 to 5, and other maltooligosaccharides having glucose polymerizations of 8 or higher by intermolecular α-1,4 transglycosylation; and simultaneously catalyzes intramolecular α-1,6 transglycosylation to form $ICG_5$ from maltooligosaccharide having a glucose polymerization degree of 7 (maltoheptaose) after cleaving the substrate by maltopentaose unit and to form $ICG_5$ and $ICG_6$ from maltooligosaccharides having glucose polymerization degrees of 8 or higher after cleaving the substrates by maltopentaose and maltohexaose units.

From the results described above, the mechanism of ICM-forming reaction by ICM-forming enzyme of the present invention was estimated as follows:

(1) The enzyme acts on α-1,4 glucan having a glucose polymerization degree of 3 or higher as the substrate and forms various maltooligosaccharides different in glucose polymerization degree by catalyzing intermolecular α-1,4 transglycosylation transferring a series of maltooligosaccharides (disproportionation reaction).

(2) In the case of acting on α-1,4 glucan having a glucose polymerization degree of 7 (maltoheptaose), the enzyme hydrolyzes the substrate by a maltopentaose unit from the non-reducing end of the substrate and catalyses a cyclization reaction intramolecularly transferring the C-1 position of the reducing end glucose of maltopentaose to the C-6 hydroxyl group of non-reducing end glucose of the same maltopentaose to form $ICG_5$ and maltose.

(3) In the case of acting on α-1,4 glucans having glucose polymerization degrees of 8 or higher, the enzyme hydrolyzes the substrate by maltopentaose or maltohexaose unit from the non-reducing end of the substrate and catalyses a cyclization reaction intramolecularly transferring the C-1 position of the reducing end glucose of maltopentaose or maltohexaose to the C-6 hydroxyl group of non-reducing end glucose of the same maltopentaose or maltohexaose to form $ICG_5$ and $ICG_6$ and α-1,4 glucan whose glucose polymerization degree is reduced by 5 or 6.

Experiment 11

Formation of ICM from Various Substrates

Formation of ICM by the action of ICM-forming enzyme of the present invention was investigated using various saccharides as substrates. Maltohexaose, maltoheptaose, amylose, soluble starch, "PINEDEX #100", a partial starch hydrolyzate commercialized by Matsutani Chemical Industries Co., Ltd., Hyogo, Japan, or glycogen from corn, commercialized by Q.P. Corporation, Tokyo, Japan, was prepared into a solution.

Each solution (concentration: 1.0% (w/v)) was admixed with acetate buffer (pH 6.0) and $CaCl_2$ to give final concentrations of 20 mM and 1 mM, further admixed with one unit/g-substrate, on a dry solid basis, of the purified preparation of ICM-forming enzyme, obtained by the method in Experiment 5, and followed by the enzyme reaction at 45° C. and pH 6.0 for 48 hours. The reaction was stopped by heating the reaction mixture at 100° C. for 10 min. After treating the reaction mixture with α-glucosidase and glucoamylase by the same manner in Experiment 1, the amount of ICM was determined by HPLC and ICM content of the reaction mixture was measured. The results are in Table 8.

TABLE 8

| Substrate | ICM content (%) | |
|---|---|---|
| | $ICG_5$ | $ICG_6$ |
| Maltohexaose | 10.7 | 2.9 |
| Maltoheptaose | 13.1 | 3.1 |
| Amylose | 24.8 | 4.0 |
| Soluble starch | 23.8 | 4.1 |
| Partial starch hydrolyzate | 16.9 | 3.4 |
| Glycogen | 11.5 | 3.1 |

As is evident from the results in Table 8, $ICG_5$ and $ICG_6$ were formed from all substrate tested by the action of ICM-forming enzyme. In the case of using maltohexaose as a substrate, the total content of $ICG_5$ and $ICG_6$ was low about 14%. However, the content was the highest to about 29% in the case of using amylose as a substrate and higher in the case of using soluble starch and partial starch hydrolyzate in that order.

Experiment 12

Relationship of ICM-Forming Reaction and the Reducing Power of the Reaction Products An aqueous solution containing 1.0% (w/v) of amylose was admixed with acetate buffer (pH 6.0) and $CaCl_2$ to give final concentrations of 20 mM and 1 mM, respectively. The resulting substrate solution was admixed with one unit/g-solid, on a dry solid basis, of the purified enzyme preparation of ICM-forming enzyme, obtained by the method in Experiment 5, and followed by the reaction at 45° C. and pH 6.0. A reaction mixture at the zero-time reaction was obtained by the steps of sampling the aliquot of the reaction mixture just after adding the enzyme, stopping the reaction by heating at about 100° C. for 10 min, and cooling the sample. Successively, aliquots of the reaction mixture were withdrawn at the reaction time of 1, 2, 3 and 4 hours, and the samples were immediately stopped the reactions by heating at about 100° C. for 10 min, and cooled to make into reaction mixtures reacted for 1, 2, 3, and 4 hours. The amount of reducing sugars and total sugars in the resulting reaction mixtures were measured by the Somogyi-Nelson method and Anthrone-sulfuric acid method. Reducing power of the reaction mixture was defined as the ratio of the amount of reducing sugars to the amount of total sugars and expressed in percentage. Further, the contents of ICM in the reaction mixtures were measured by the steps of treating the reaction mixtures with α-glucosidase and glucoamylase in the same manner in Experiment 1 and measuring the amounts of ICM by HPLC. The results are in Table 9.

TABLE 9

| Reaction time (hour) | Reducing power (%) | ICM content (%) | |
|---|---|---|---|
| | | $ICG_5$ | $ICG_6$ |
| 0 | 6.9 | 0.0 | 0.0 |
| 1 | 7.1 | 7.8 | 0.0 |
| 2 | 7.0 | 11.7 | 0.5 |
| 3 | 7.0 | 14.4 | 0.6 |
| 4 | 6.9 | 16.2 | 0.7 |

As is evident from the results in Table 9, when ICM were formed by allowing ICM-forming enzyme to act on soluble starch, it was revealed that the reducing powers of the reaction mixture were slightly increased by about 0.1% even when the contents of ICM were 10% or higher. These results indicate that ICM-forming enzyme of the present invention substantially catalyzes transferring and cyclizing reaction and hardly catalyzes hydrolytic reaction. It was also revealed that products with low reducing power can be obtained by lowering the reducing power of starches or starch hydrolyzates, i.e., the DE (dextrose equivalent) value before the reaction because the reducing power is hardly increased, when ICM are formed by allowing the enzyme to act on starches or starch hydrolyzates.

Experiment 13

Effect of the Addition of Isoamylase or Pullulanase on the Formation of ICM

An aqueous solution containing 1% (w/v) of "PINEDEX #100", a partial starch hydrolyzate commercialized by Matsutani Chemical Industries Co., Ltd., Hyogo, Japan, was admixed with acetate buffer (pH 5.5) and $CaCl_2$ to give final concentrations of 20 mM and 1 mM, respectively. The resulting substrate solution was admixed with one unit/g-substrate, on a dry solid basis, of the purified preparation of ICM-forming enzyme, obtained by the method in Experiment 5, and zero, 125, 250, 500, 1,250 or 2,500 units/g-substrate, on a dry solid basis, of isoamylase commercialized by Hayashibara Biochemical Laboratories Inc., Okayama, Japan, and followed by the enzyme reaction at 45° C. and pH 5.5 for 24 hours. The reaction was stopped by heating the reaction mixture at 100° C. for 10 min. Successively, after treating the reaction mixture with α-glucosidase and glucoamylase by the same manner in Experiment 1, the amounts of ICM were determined by HPLC and ICM contents of the reaction mixture were measured. In place of isoamylase, zero, 1.3, 2.7, 5.3, 13.3, and 26.7 units/g-substrate, on a dry solid basis, of pullulanase were added to the substrate solution and similarly investigated by the same procedures, and then determined the contents of ICM. These results are in Tables 10 and 11, respectively.

TABLE 10

| Amount of isoamylase (Units) | ICM content (%) | |
|---|---|---|
| | $ICG_5$ | $ICG_6$ |
| 0 | 21.1 | 1.8 |
| 125 | 23.5 | 1.8 |
| 250 | 24.4 | 1.9 |
| 500 | 25.3 | 2.0 |
| 1250 | 25.8 | 2.0 |
| 2500 | 25.9 | 2.0 |

TABLE 11

| Amount of pullulanase (Units) | ICM content (%) | |
|---|---|---|
| | $ICG_5$ | $ICG_6$ |
| 0.0 | 21.1 | 1.8 |
| 1.3 | 24.9 | 2.0 |
| 2.7 | 25.4 | 2.0 |
| 5.3 | 26.0 | 2.1 |
| 13.3 | 26.4 | 2.2 |
| 26.7 | 26.6 | 2.3 |

As is evident from the results in Tables 10 and 11, it was revealed that ICM content in the reaction mixture is increased by adding isoamylase or pullulanase.

Experiment 14

Effect of the DE Value of Liquefied Starch on the Formation of ICM

Corn starch was prepared into 2% (w/w) suspension and admixed with calcium carbonate to give a concentration of 0.1% (w/w). After adjusting pH to 6.0, the resulting suspension was further admixed with "THERMAMYL 60L", an α-amylase commercialized by Novozymes Japan, Chiba, Japan, to give a concentration of 0.2, 0.4, 0.6, 1.0, 1.5, or 2.0% (w/w) per gram starch. These solutions were reacted at 95° C. for 10 min, autoclaved at 120° C., and immediately cooled to about 40° C. to obtain six kinds of liquefied starch solutions with DE values of 3.1 to 20.4, as shown in Table 12. Each liquefied starch solution was adjusted a final concentration of 1% (w/w), admixed with one unit/g-solid of the purified preparation of ICM-forming enzyme, obtained by the method in Experiment 5, and followed by the reaction at 45° C. and pH 6.0 for 48 hours. The reaction was stopped by boiling the reaction mixture for 10 min. To measure the amounts of ICM in the boiled reaction mixture, the reaction mixture was admixed with α-glucosidase and glucoamylase with the same manner in Experiment 1 and followed by the reaction. The ICM contents in the resulting reaction mixture were obtained by measuring the amounts of ICM by HPLC. The results are in Table 12.

TABLE 12

| Amount of α-amylase (w/w %/g-starch) | DE | ICM content (%) | |
|---|---|---|---|
| | | $ICG_5$ | $ICG_6$ |
| 0.2 | 3.1 | 17.1 | 3.5 |
| 0.4 | 4.8 | 13.5 | 2.9 |
| 0.6 | 7.9 | 11.8 | 2.7 |
| 1.0 | 12.6 | 10.1 | 2.6 |

TABLE 12-continued

| Amount of α-amylase | | ICM content (%) | |
|---|---|---|---|
| (w/w %/g-starch) | DE | $ICG_5$ | $ICG_6$ |
| 1.5 | 17.4 | 8.3 | 2.4 |
| 2.0 | 20.0 | 6.3 | 1.8 |

As is evident from the results in Table 12, ICM formation by ICM-forming enzyme of the present invention was influenced by the DE value of liquefied starch. It was revealed that ICM content in the reaction mixture was increased by decreasing DE value, in other word, decreased by increasing DE value. Particularly, it was revealed that DE value of the liquefied starch is preferable to, usually, about 20 or lower, desirably, about 8 or lower, more desirably, about 5 or lower.

Experiment 15

Thermal Stability of ICM $ICG_5$, prepared from soluble starch by the method in Experiment 11 and purified to give a purity of 100% by the method in Experiment 1, was used as material. An aqueous $ICG_5$ solution with a concentration of 5% (w/v) was prepared by dissolving $ICG_5$ in deionized water. Then, 8 ml each of the resulting solution was pored into a glass tube, sealed closely, and then heated at 120° C. for 30 to 90 min. After cooling the solution, the degree of coloring of the solution was measured. Further, the purity of $ICG_5$ in the solution was measured by HPLC. The degree of coloring was defined as an absorbance at 480 nm using a 1 cm-cell. The results are in Table 13.

TABLE 13

| Heating time (min) | Degree of coloring (A480 nm) | Purity (%) |
|---|---|---|
| 0 | 0.00 | 100 |
| 30 | 0.00 | 100 |
| 60 | 0.00 | 100 |
| 90 | 0.01 | 100 |

As is evident from the results in Table 13, aqueous solutions of $ICG_5$ were not colored, and the purities of $ICG_5$ were not decreased even in the case of heating to a high temperature, 120° C. It was revealed that $ICG_5$ is stable under the heating condition.

Experiment 16 pH Stability of ICM $ICG_5$, used in Experiment 15, was dissolved in various buffers to make into nine kinds of aqueous solutions containing 4% (w/v) of $ICG_5$, adjusted to pH 2 to 10, as shown in Table 14. Eight milliliters of each solution was put in a glass tube, sealed and then heated at 100° C. for 24 hours. After cooling the solution, the degree of coloring and the purity of $ICG_5$ of each solution were measured in the same manner in Experiment 15. The results are in Table 14.

TABLE 14

| pH | Buffer | Degree of coloring (A480 nm) | Purity (%) |
|---|---|---|---|
| 2.0 | Acetate | 0.00 | 0 |
| 3.0 | Acetate | 0.00 | 34.9 |
| 4.0 | Acetate | 0.00 | 89.9 |
| 5.0 | Acetate | 0.00 | 99.4 |
| 6.0 | Acetate | 0.00 | 100 |
| 7.0 | Borate | 0.00 | 100 |
| 8.0 | Ammonium | 0.00 | 100 |
| 9.0 | Ammonium | 0.01 | 100 |
| 10.0 | Ammonium | 0.01 | 99.6 |

As is evident from the results in Table 14, $ICG_5$ was substantially not hydrolyzed in a pH range of 5 to 10 even in the case of heating at 100° C. for 24 hours. It was revealed that $ICG_5$ is stable in a wide range of slightly acidic pH to alkaline pH. However, $ICG_5$ was slightly hydrolyzed at pH 4 and hydrolyzed 50% or more at pH 3. Further, $ICG_5$ was completely hydrolyzed at pH 2 and disappeared.

Experiment 17

Amino-Carbonyl Reaction $ICG_5$, used in Experiment 15 and commercially available super high-grade glycine were dissolved in deionized water, and then admixed with phosphate buffer to make into an aqueous $ICG_5$ solution containing 5% (w/v) of $ICG_5$ and 1% (w/v) glycine, adjusted to pH 7.0. As a control, an aqueous α-cyclodextrin (α-CD) solution containing α-CD and glycine was prepared in the same manner using α-CD in place of $ICG_5$. Four milliliters each of the solution was put in a glass tube, sealed and then heated at 120° C. for 30, 60, or 90 min. After cooling the solutions in ambient temperature, the degrees of coloring of the solutions were measured to estimate the degree of amino-carbonyl reaction. As a blank test, a solution containing glycine only was heated in the same manner. The degree of coloring was defined as an absorbance at 480 nm using a 1 cm-cell after subtracting the absorbance of the blank test. The results are in Table 15.

TABLE 15

| Heating time (min) | Degree of coloring (A480 nm) | |
|---|---|---|
| | $ICG_5$ | α-CD |
| 0 | 0.00 | 0.02 |
| 30 | 0.00 | 0.02 |
| 60 | 0.00 | 0.03 |
| 90 | 0.00 | 0.02 |

As is evident from the results in Table 15, the $ICG_5$ solution showed no increase of coloring, revealing that $ICG_5$ is a stable saccharide which hardly causes coloring and browning even when heating in the presence of glycine and has a low amino-carbonyl reactivity, as in the case of α-CD.

Experiment 18

Amino-Carbonyl Reaction $ICG_5$ used in Experiment 15 and commercially available polypeptone, commercialized by Nihon Pharmaceutical Co., Ltd., Tokyo, Japan, were dissolved in deionized water to make into an aqueous solution containing 5% (w/v) of $ICG_5$ and 5% (w/v) of polypeptone. As a control, an aqueous solution containing α-CD and polypeptone was prepared in the same manner using α-CD in place of $ICG_5$. Four milliliters each of the solution was put in a glass tube, sealed and then heated at 120° C. for 30, 60, or 90 min. After cooling the solutions in ambient temperature, the degrees of coloring of the solutions were measured to estimate the degree of amino-carbonyl reaction. As a blank test, a solution containing polypeptone only was heated in the same manner. The degree of coloring was defined as an absorbance at 480 nm using a 1 cm-cell after subtracting the absorbance of the blank test. The results are in Table 16.

TABLE 16

| Heating time (min) | Degree of coloring (A480 nm) | |
|---|---|---|
| | $ICG_5$ | α-CD |
| 0 | 0.00 | 0.01 |
| 30 | 0.02 | 0.03 |
| 60 | 0.02 | 0.04 |
| 90 | 0.02 | 0.06 |

As is evident from the results in Table 16, the $ICG_5$ solution showed slight increase of coloring, revealing that $ICG_5$ is a stable saccharide which hardly causes coloring and browning even when heating in the presence of glycine and has a low amino-carbonyl reactivity, as in the case of α-CD.

Experiment 19

Clathrating Action of ICM $ICG_5$ used in Experiment 15, was dissolved in deionized water to make into an aqueous solution containing 20% (w/v) of $ICG_5$. Twenty milliliters of the aqueous solution was admixed with 3-folds amount, on a molar basis to $ICG_5$, of either of four kinds of short chain alcohols, i.e., methanol, ethanol, propanol, and butanol; four kinds of short chain fatty acids, i.e., acetic acid, propionic acid, n-butyric acid, and n-valeic acid; and four kinds of aromatic compounds, i.e., benzyl alcohol, phenethyl alcohol, 4-phenyl-1-propanol, and o-cresol; and then stirred the mixture to homogeneity for allowing $ICG_5$ to clathrate the compound. Successively, each solution was filtrated, and the resulting filtrate was freeze-dried to remove unclathrated compound. In order to measure the amount of compound clathrated in the freeze-dried product, the amount of each compound in each freeze-dried product was determined by gas-chromatography. Alpha-CD was used as a control and subjected to the similar test. The results are in Table 17.

TABLE 17

| | | Amount of compound clathrated (mg/g-freeze-dried product) | |
|---|---|---|---|
| Objective compound | | $ICG_5$ | α-CD |
| Short chain alcohols | Methanol | 33.5 | 16.7 |
| | Ethanol | 57.6 | 36.7 |
| | Propanol | 69.2 | 66.8 |
| | Butanol | 82.7 | 79.5 |
| Short chain fatty acids | Acetic acid | 82.4 | 15.1 |
| | Propionic acid | 91.4 | 16.6 |
| | n-Butyric acid | 69.9 | 13.2 |
| | n-Valeic acid | 48.3 | 45.0 |
| Aromatic compounds | Benzyl alcohol | 61.9 | 165.7 |
| | Phenethyl alcohol | 10.0 | 144.4 |
| | 4-Phenyl 1-propanol | 225.2 | 171.5 |
| | o-Cresol | 151.5 | 49.5 |

As is evident from the results in Table 17, it was revealed that $ICG_5$ has an activity of clathrating various compounds such as short chain alcohols, short chain fatty acids and aromatic compounds. In the cases of methanol, ethanol, acetic acid, propionic acid, and n-butyric acid, the amounts of compounds clathrated by $ICG_5$ were higher than those in α-CD. Although $ICG_5$ has an activity of clathrating aromatic compounds, the amount of them clathrated were different depending on kinds of compounds.

Experiment 20

Digestibility of ICM

According to the method of Okada et al., described in *Journal of Japanese Society of Nutrition and Food Sciences*, vol. 43, 23-29 (1990), the digestibility of ICM by salivary α-amylase, artificial gastric juice, pancreas amylase, and small intestinal enzymes were investigated using $ICG_5$, used in Experiment 15. Alpha-, α- and γ-cyclodextrin, which have been known as cyclic saccharides, were used as controls. The results are in Table 18. In Table 18, the digestion (%) means a value calculated by the formula:

Digestion (%)=(The amount of reducing saccharides/ The amount of the total saccharides)×100

, in respective reaction described above.

TABLE 18

| | Digestion (%) | | | |
|---|---|---|---|---|
| Digestive enzyme | $ICG_5$ | α-CD* | β-CD | γ-CD |
| Salivary α-amylase | 0 | 0 | 0 | 0.1 |
| Artificial gastric juice | 0 | 0 | 0 | 0 |
| Pancreas α-amylase | 0 | 0 | 0.2 | 5.4 |
| Small intestinal enzymes | 0.2 | 0.2 | 1.1 | 57.4 |

*CD: Cyclodextrin

As is evident from the results in Table 18, $ICG_5$ was substantially not digested by either of salivary amylase, artificial gastric juice, pancreas amylase and small intestinal enzymes as in the cases of α- and β-cyclodextrin. While, γ-cyclodextrin was partially digested by pancreas α-amylase and small intestinal enzymes. It was revealed that $ICG_5$ is one of hardly digestive saccharides.

Experiment 21

Acute Toxicity Test

By using mice, $ICG_5$ used in Experiment 15 was orally administrated to the mice for its acute toxicity test. As a result, it was revealed that $ICG_5$ is a safe substance with a relatively low toxicity, and that no mouse died even when administrated with it at the highest possible dose. Though not so accurate, the value of $LD_{50}$ of $ICG_5$ was 5 g/kg-mouse weight or higher.

The followings explain the present invention in detail. However, the present invention is not restricted by them.

Example 1

According to the method in Experiment 1, *Bacillus circulans* AM7 (FERM BP-10111) was cultivated to obtain the seed culture. Successively, a liquid medium containing 1.5% (w/v) of "PINE-DEX #4", a partial starch hydrolyzate commercialized by Matsutani Chemical Industry Co., Ltd., Hyogo, Japan), 0.5% (w/v) of "POLYPEPTONE", a yeast extract commercialized by Nihon Pharmaceutical Co., Ltd., Tokyo, Japan, 0.1% (w/v) of "YEAST EXTRACT S", a yeast extract commercialized by Nihon Pharmaceutical Co., Ltd., Tokyo, Japan, 0.1% (w/v) of dipotassium phosphate, 0.06% (w/v) of sodium phosphate dihydrate, 0.05% (w/v) of magnesium sulfate heptahydrate, 0.3% (w/v) of calcium carbonate, and water was placed in a 30-L fermenter in an amount of about 20 L, sterilized by heating, and cooled to 27° C. Then, 1% (v/v) of the liquid medium of the seed culture was inoculated into the liquid medium, and the bacterium was cultured with keeping a temperature at 27° C. and pH at 5.5 to 8.0 for 96 hours under aeration-agitation conditions. After completion of the cultivation, cells were removed by filtrating with SF-membrane and about 18 L of the resulting culture filtrate was collected. Further, the filtrate was concentrated using a UF-membrane and about 1 L of a concentrated enzyme solution, containing 0.41 units/ml of ICM-forming enzyme activity, was obtained.

Example 2

A potato starch was prepared into a 1% (w/v) starch suspension, admixed with calcium chloride to give a final concentration of 1 mM, adjusted to pH 6.0, and then gelatinized by heating at 95° C. for about 20 min. After cooling the resulting substrate solution to about 40° C., the concentrated enzyme solution containing ICM-forming enzyme, obtained by the method in Example 1, was admixed with the substrate solution to give a ratio of 2.44 ml (about one unit)/g-dry solid of starch, and followed by the enzymatic reaction at pH 6.0 and 40° C. for 48 hours. After keeping to 95° C. for 30 min, the reaction mixture was cooled and filtrated. According to conventional manner, the resulting filtrate was decolored with activated charcoal, desalted and purified with ion exchangers in H- and OH-forms. Then, the purified solution was concentrated to give a concentration of 65% (w/v) and a syrup containing ICM was obtained in a yield of about 90%, on a dry solid basis. The syrup contained, on a dry solid basis, 27.5% (w/w) of ICM and 72.5% (w/w) of other saccharides. Since the product has a relatively low reducing power and adequate viscosity, it can be advantageously used in various compositions such as foods and beverages, cosmetics, and pharmaceuticals as a sweetener, taste-improving agent, quality-improving agent, syneresis-preventing agent, stabilizer, discoloration-preventing agent, excipient, clathrating agent, and base for powderization.

Example 3

A tapioca starch was prepared into a 1% (w/v) starch suspension, admixed with calcium carbonate to give a concentration of 0.1% (w/v), adjusted to pH 6.5, and admixed with 0.2%/g-starch of "THERMAMYL 60 L", an α-amylase commercialized by Novo Industries A/S, Copenhagen, Denmark, and then incubated at 95° C. for 10 min. After autoclaving at 120° C. for 20 min, the reaction mixture was cooled rapidly to about 40° C. to make into a liquefied starch solution with a DE of about 3. The liquefied starch solution was admixed with 2.44 ml (about one unit)/g-dry solid starch of the concentrated enzyme solution containing ICM-forming enzyme, obtained by the method in Example 1, and 1,000 units/g-dry solid starch of isoamylase commercialized by Hayashibara Biochemical Laboratories Inc., Okayama, Japan, and followed by the enzymatic reaction at pH 6.0 and 40° C. for 48 hours. After heating to 95° C. for 30 min, the reaction mixture was cooled and filtrated. According to conventional manner, the resulting filtrate was decolored with activated charcoal, desalted and purified with ion exchangers in H- and OH-forms. Then, the purified solution was concentrated to give a concentration of 60% (w/v) and a syrup containing 31.5% (w/w), on a dry solid basis, of ICM was obtained. The syrup as a saccharide solution was subjected to a column chromatography using "AMBERLITE CR-1310" (Na-form), a strongly acidic cation-exchange resin commercialized by Organo Corporation, Tokyo, Japan. The resin was packed into four jacketed stainless steel columns having a diameter of 5.4 cm, which were then cascaded in series to give a total gel bed depth of 20 m. Under the conditions of keeping the inner column temperature at 60° C., the saccharide solution was fed to the columns in a volume of 5% (v/v) and fractionated by feeding to the columns hot water heated to 60° C. at an SV (space velocity) of 0.13 to obtain high ICM content fractions. While monitoring the saccharide composition of elute by HPLC, and then the low molecule fractions including the saccharide fraction comprising ICM were collected and the fractions were purified, concentrated and spray-dried. As a result, a powdery product comprising ICMs was obtained in a yield of about 54%, on a dry solid basis. The product contained, on a dry solid basis, 51.5% of ICM and 48.5% of other saccharides. Since the product has a relatively low reducing power, it can be advantageously used in various compositions such as foods and beverages, cosmetics, and pharmaceuticals as a sweetener, taste-improving agent, quality-improving agent, syneresis-preventing agent, stabilizer, discoloration-preventing agent, excipient, and clathrating agent.

Example 4

A corn starch was prepared into a about 1% (w/v) starch suspension, admixed with calcium carbonate to give a concentration of 0.1% (w/v), adjusted to pH 6.0, and admixed with 0.2%/g-starch of "NEOSPITASE", an α-amylase commercialized by Nagase ChemteX Corporation, Osaka, Japan, and then incubated at 85° C. to 95° C. for 20 min. After autoclaving at 120° C. for 20 min, the reaction mixture was cooled rapidly to about 40° C. to make into a liquefied starch solution with a DE of about 3. The liquefied starch solution was admixed with 2.44 ml (about one unit)/g-dry solid starch of the concentrated enzyme solution containing ICM-forming enzyme, obtained by the method in Example 1, and 1,000 units/g-dry solid starch of isoamylase commercialized by Hayashibara Biochemical Laboratories Inc., Okayama, Japan, and followed by the enzymatic reaction at pH 6.0 and 40° C. for 48 hours. After heating to 95° C. for 30 min, the reaction mixture was cooled to about 50° C. and adjusted to pH 5.0. Then, the reaction mixture was admixed with 1,000 units/g-starch of "TRANSGLUCOSIDASE L-AMANO", an α-glucosidase commercialized Amano Enzyme Inc., Aichi, Japan, and 100 units/g-starch of "GLUCOZYME", a glucoamylase commercialized by Nagase ChemteX Corporation, Osaka, Japan, and followed by the enzyme reaction at pH 5.0 and 50° C. for 16 hours. After heating the reaction mixture to 95° C. and keeping for 30 min, it was cooled and filtrated. According to conventional manner, the resulting filtrate was decolored with activated charcoal, desalted and purified with ion exchangers in H- and OH-forms. Then, the purified solution was concentrated to give a concentration of 60% (w/v) and a syrup comprising ICM was obtained in a yield of about 95%, on a dry solid basis. The product contained, on a dry solid basis, 32.6% (w/w) of ICM, 63.0% (w/w) of glucose, and 4.4% (w/w) of other saccharides. Since the product has a mild sweetness and adequate viscosity, it can be advantageously used in various compositions such as foods and beverages, cosmetics, and pharmaceuticals as a sweetener, taste-improving agent, quality-improving agent, syneresis-preventing agent, stabilizer, discoloration-preventing agent, excipient, clathrating agent, and base for powderization.

Example 5

The syrup comprising ICM, obtained by the method in Example 4, was placed in an autoclave and admixed with about 0.9% (w/w) to dry solid of Raney-nickel as catalyst, and then heated to 130° C. with stirring and hydrogenated by elevating hydrogen-pressure to 75 kg/cm$^2$ to convert reducing saccharides comprised in the syrup into sugar alcohols. After removing Raney-nickel, the resulting reaction mixture was purified, concentrated, dried in vacuo, and pulverized according to conventional methods and a powdery product comprising ICM was obtained in a yield of about 90%, on a dry solid basis. The product contained, on a dry solid basis, 32.5% of ICM, 63.2% of sorbitol, and 4.3% of other sugar alcohols. Since the product substantially shows no reducing power and hardly causes amino-carbonyl reaction, it can be advantageously used in various compositions such as foods and beverages, cosmetics, and pharmaceuticals as a sweetener, taste-improving agent, quality-improving agent, syneresis-preventing agent, stabilizer, discoloration-preventing agent, excipient, and clathrating agent.

Example 6

Sweetener

To 0.8 part by weight of a powdery product comprising ICM, obtained by the method in Example 3, 0.2 part by weight of "TREHA®", hydrous crystalline trehalose commercialized by Hayashibara Shoji Inc., Okayama, Japan, 0.01 part by weight of "αG-SWEET", α-glycosyl-stevioside commercialized by Toyo Sugar Refining Co., Ltd, Tokyo, Japan, and 0.01 part by weight of "ASPERTAME", L-aspartyl-L-phenylalanine-methyl-ester commercialized by Ajinomoto Co., Inc., Tokyo, Japan, were mixed to homogeneity and granulated using a granulator to make into a sweetener in a granule form. The product has a good sweetness and shows about 2-folds higher sweetness than that of sucrose. Since the product is stable with no fear of deterioration under the preservation at an ambient temperature, it can be advantageously used as a sweetener.

Example 7

Hard Candy

Fifty parts by weight of a syrup comprising ICM, obtained by the method in Example 4, was admixed with 100 parts by weight of sucrose solution with a sucrose concentration of 55% (w/v) with heating. Then, the mixture was concentrated under a reduced pressure to give a moisture content of less than 2%. The resulting concentrate was admixed with 0.6 part by weight of citric acid and suitable amounts of lemon flavor and coloring, shaped into hard candy according to conventional method. The product shows a satisfactory non-adhesion, taste, flavor, and hardly causes the crystallization of sucrose. The product is a high quality hard candy with low hygroscopicity and no fluidity.

Example 8

Chewing Gum

Three parts by weight of gum base was softened by heating and melting, and then admixed with two parts by weight of anhydrous maltitol, two parts of xylitol, two parts by weight of a powdery product comprising ICM, obtained by the method in Example 5, one part by weight of hydrous crystalline trehalose, and suitable amounts of flavor and colorings. The mixture was kneaded by a roll, shaped and packed to make into chewing gum. Since the product has a satisfactory texture, taste, and flavor, it is preferable as a chewing gum with a low-cariogenicity, and low calorie.

Example 9

Sweetened Condensed Milk

Four parts by weight of a syrup comprising ICM, obtained by the method in Example 2, and two parts by weight of sucrose were dissolved in 100 parts by weight of material milk. The resulting mixture was sterilized by heating with a plate heater, concentrated to give a concentration of 70%, and then packed in a can under a sterile condition to make into a product. Since the product has a mild sweetness and good flavor, it can be advantageously used for seasoning fruits, coffee, cocoa, black tea, and the like.

Example 10

Lactic Acid Bacteria Beverage

One hundred seventy-five parts by weight of skim milk, 100 parts by weight of a powdery product comprising ICM, obtained by the method in Example 3, and "NYUKA-OLIGO", a lactosucrose high content powder commercialized by Hayashibara Shoji Inc., Okayama, Japan, were dissolved into 1,500 parts by weight of water, and then the resulting mixture was sterilized at 65° C. for 30 min. After cooling the mixture to 40° C., 30 parts by weight of a lactic acid bacterium was inoculated to the mixture as a starter according to conventional method, and cultured at 37° C. for eight hours to obtain a lactic acid bacteria beverage. The product has a satisfactory flavor and keeps the lactic acid bacterium stably because it comprises oligosaccharides and ICM. Further, the product is preferably used as a lactic acid bacteria beverage having a growth-promoting activity for bifidobacteria and a function-regulating activity for intestine.

Example 11

Powdery Juice

To 33 parts by weight of a powdery orange juice, produced by a spray-drying method, 50 parts by weight of a powdery product comprising ICM, obtained by the method in Example 5, 10 parts by weight of anhydrous crystalline maltitol, 0.65 part by weight of anhydrous citric acid, 0.1 part by weight of malic acid, 0.2 part by weight of 2-O-α-glucosyl-L-ascorbic acid, 0.1 part by weight of sodium citrate, 0.5 part by weight of pullulan, and suitable amount of powdery flavor were mixed with stirring and the resulting powdery mixture was pulverized to make into a fine powdery product. Then, the powdery product was subjected to a fluidized bed granulator and its exhaust temperature was set to 40° C. A suitable amount of a syrup comprising ICM, obtained by the method in Example 2, was sprayed on the powdery product and granulated for 30 min and the resulting product was weighted and packed to make into a product. The product is a powdery juice with a fruit-juice content of about 30%. Since the product shows no strange taste and smell, it has a high quality and commercial value as a low-calorie juice.

Example 12

Custard Cream

One hundred parts by weight of corn starch, 100 parts by weight of a syrup comprising ICM, obtained by the method in Example 2, 60 parts by weight of hydrous crystalline trehalose, 40 parts by weight of sucrose, and one part by weight of sodium chloride were mixed well, and then 280 parts by weight of whole egg was further admixed with the mixture. Successively, 1,000 parts by weight of boiled milk was gradually admixed with the resulting mixture and the resulting solution was continuously stirred on an open flame. The heating was stopped at the point that corn starch was completely gelatinized to give a transparency. After cooling the mixture, a suitable amount of vanilla essence was admixed with the mixture, weighted, and packed to make into a custard cream product. The product is a high quality custard cream with a satisfactory gloss and flavor, whose retrogradation of starch is inhibited.

Example 13

Ham

To 1,000 parts by weight of dark meat of pork, 15 parts by weight of sodium chloride and three parts by weight of potassium nitrate were penetrated and then preserved for one day in a refrigerated room. The resulting pork was soaked into a pickled solution composed of 500 parts by weight of water, 100 parts by weight of sodium chloride, three parts by weight of potassium nitrate, 40 parts by weight of a powdery product comprising ICM, obtained by the method in Example 5, and spices, for seven days in a refrigerated room. Successively, according to conventional method, the soaked pork was washed with cold water, rolled with a string, smoked, cooked, cooled and packed to make into a ham product. The product is a high-quality ham with a satisfactory color and flavor.

Example 14

Powdery Peptide Product

To one part by weight of "HI-NUTE S", 40% soybean peptides solution for foods, commercialized by Fuji Oil Co., Ltd., Osaka, Japan, two parts by weight of a powdery product comprising ICM, obtained by the method in Example 3, was mixed and the resulting mixture was put into aplastic tray, dried at 50° C. under a reduced pressure, and pulverized to make into a powdery peptide product. The product has a satisfactory flavor and is useful as a material for premix, low-calorie confectionaries for ice dessert. Further, the product is useful as a less-digestive dietary fiber and antiflaturent for a fluid diet for oral- or tube-intake.

Example 15

Cosmetic Cream

According to conventional method, two parts by weight of polyoxyethylenglycol mono-stearate, five parts by weight of self-emulsified glycerin mono-stearate, two parts by weight of a powdery product comprising ICM, obtained by the method in Example 5, one part by weight of "αG-RUTIN", α-glucosyl rutin, commercialized by Hayashibara Inc., Okayama, Japan, one part by weight of liquid paraffin, 10 parts by weight of glycerin-trioctanoate and a suitable amount of preservative were mixed and dissolved by heating. The resulting mixture was further admixed with two parts by weight of L-lactic acid, five parts by weight of 1,3-butylen glycol, and 66 parts by weight of purified water, and the resulting mixture was emulsified using a homogenizer. The homogenized mixture was further admixed with a suitable amount of flavor and stirred to make into a cosmetic cream. The product has an antioxidative activity and satisfactory stability, and can be advantageously used as a sunburn preventive, skin-care agent and whitening agent for skin.

Example 16

Toothpaste

Forty-five parts by weight of calcium monohydrogen phosphate, 1.5 parts by weight of sodium lauryl sulfate, 25 parts by weight of glycerin, 0.5 part by weight of polyoxyethylene sorbitan laurate, 10 parts by weight of a powdery products comprising ICM, obtained by the method in Example 3, 0.02 part by weight of saccharin, and 18 parts by weight of water were mixed to make into a toothpaste. The product is toothpaste whose bad taste is improved and shows a satisfactory availability without losing the washing property of surfactant.

Example 17

Solid Agent for a Fluid Diet

One hundred parts by weight of a syrup comprising ICMs, obtained by the method in Example 2, 200 parts by weight of hydrous crystalline trehalose, 200 parts by weight of a maltotetraose high content powder, 270 parts by weight of powdery egg yolk, 209 parts by weight of skim milk, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 parts by weight of vitamin E acetate, and 0.04 part by weight of nicotinic acid-amide were mixed to make into a composition. Twenty-five grams each of the composition was packed into a damp proof laminate pouch, and the pouch was heat-sealed to make into a product. It can be advantageously used for supplying energy to living bodies as a fluid diet to regulate the function of intestine by taking orally or through tube into nasal cavity, stomach, and intestine.

Example 18

Ointment for Curing Wound

One hundred parts by weight of a powdery product comprising ICM, obtained by the method in Example 5, 300 parts by weight of maltose, 50 parts by weight of a methanol solution containing three parts by weight of iodine, and 200 parts by weight of 10% (w/v) aqueous pullulan solution were mixed to make into an ointment for curing wound with an adequate extendability and adhesive property. The product is an ointment with a high marketability and less change over time. Since iodine in the product has an antimicrobial activity and maltose in the product acts as an energy-supplement for cells, the curing period is shortened and wound surface is cured completely.

INDUSTRIAL APPLICABILITY

According to the present invention, novel ICM having a structure represented by General Formula 1, which has been unknown, can be provided in a large amount by producing the ICM using ICM-forming enzyme. The present invention, enabling to provide novel ICM, contributes to various fields such as foods and beverages, cosmetics, and pharmaceuticals. The present invention, having these outstanding functions and effects, is a significantly important invention that greatly contributes to this art.

$$\text{Cyclo}\{\rightarrow 6)\text{-}[\alpha\text{-D-Glcp-}(1\rightarrow 4)]_n\text{-}\alpha\text{-D-Glcp-}(1\rightarrow\} \quad \text{General Formula 1}$$

(In General Formula 1, "n" means a number of 4 or 5)

The invention claimed is:

1. An isocyclomaltooligosaccharide having a structure represented by General Formula I:

Cyclo{→6)-[α-D-Glcp-(1→4)]$_n$-α-D-Glcp-(1→} General Formula 1

(In General Formula 1, "n" means a number of 4 or 5).

2. A saccharide comprising an isocyclomaltooligosaccharide(s), which contains the isocyclomaltooligosaccharide of claim 1 and other saccharide(s).

3. The saccharide comprising isocyclomaltooligosaccharide(s) of claim 2, which is in the form of a syrup, powder, or solid.

4. A method for forming an isocyclomaltooligosaccharide(s) having a structure represented by General Formula 1 of claim 1, comprising
allowing the isocyclomaltooligosaccharide-forming enzyme or the microorganism, capable of producing an isocyclomaltooligosaccharide-forming enzyme to act on a solution containing α-1,4 glucan having a glucose polymerization degree of 3 or higher.

5. The method of claim 4, wherein said α-1,4 glucan having a glucose polymerization degree of 3 or higher is one or more saccharides selected from the group consisting of maltooligosaccharide maltodextrin, amylodextrin, amylose, amylopectin, soluble starch, liquefied starch, gelatinized starch, and glycogen.

6. A process for producing an isocyclomaltooligosaccharide(s) having a structure represented by General Formula 1 of claim 1 or a saccharide composition comprising the same, comprising
allowing the isocyclomaltooligosaccharide-forming enzyme to act on a gelatinized and/or liquefied starch solution.

7. The process of claim 6, where the DE value of said gelatinized and/or liquefied starch solution is 20 or lower.

8. The process of claim 6, comprising:
allowing isoamylase or pullulanase to act on said gelatinized and/or liquefied starch solution together with the isocyclomaltooligosaccharide-forming enzyme; and
optionally, further allowing one or more enzymes selected from the group consisting of α-amylase, β-amylase, cyclomaltodextrin glucanotransferase, glucoamylase, and α-glucosidase to act on the solution.

9. The process of claim 6, comprising:
allowing isoamylase or pullulanase to ace on said gelatinized and/or liquefied starch solution together with the isocyclomaltooligosaccharide-forming enzyme;
optionally, further allowing one or more enzymes selected from the group consisting of α-amylase, β-amylase, cyclomaltodextrin glucanotransferase, glucoamylase, and α-glucosidase to act on the solution; and
successively, subjecting the resulting reaction mixture to one or more purification methods selected from the group consisting of fractionation using a column chromatography, separation using a membrane, fermentation by a microorganism, and degradation/elimination by alkaline treatment.

10. A composition in the form of a food, beverage, cosmetic, or pharmaceutical, which is produced by incorporating the isocyclomaltooligosaccharide of claim 1.

11. A composition in the form of a food, beverage, cosmetic, or pharmaceutical, which is produced by incorporating the saccharide composition of claim 2.

* * * * *

SEQUENCE LISTING

<160> NUMBER OF SEQ ID NOS: 23

<210> SEQ ID NO 1
<211> LENGTH: 20
<212> TYPE: PRT
<213> ORGANISM: Bacillus circulans

<400> SEQUENCE: 1

```
Ala Ser Ile Gly Thr Val Thr Glu Asn Asp Thr Ile Tyr Gln Ile Met
1               5                   10                  15

Val Asp Arg Phe
            20
```

<210> SEQ ID NO 2
<211> LENGTH: 960
<212> TYPE: PRT
<213> ORGANISM: Bacillus circulans

<400> SEQUENCE: 2

```
Ala Ser Ile Gly Thr Val Thr Glu Asn Asp Thr Ile Tyr Gln Ile Met
1               5                   10                  15

Val Asp Arg Phe Asn Asp Gly Asp Ser Ser Asn Asn Ala Thr Gly Ala
            20                  25                  30

Ala Ile Arg Tyr Gly Glu Asn Ser Glu Glu Asp Phe Arg Tyr Met Lys
        35                  40                  45

Gly Gly Asp Trp Gln Gly Val Ile Asp Lys Leu Pro Tyr Ile His Asn
    50                  55                  60

Met Gly Tyr Thr Ala Ile Trp Ile Ser Pro Val Ala Glu Pro Gln Met
65                  70                  75                  80

Thr Asn Arg Glu Asn Asn Gly Thr Gly Lys Asn Thr Ala Tyr His Gly
                85                  90                  95

Tyr Asn Val Lys Asp Pro Asn Lys Ala Asn Pro Tyr Phe Gly Thr Lys
            100                 105                 110

Glu Lys Leu Lys Glu Leu Val Asp Ser Ala His Ala Leu Gly Ile Lys
        115                 120                 125

Val Ile Ile Asp Val Val Pro Asn His Ile Gly Asp Tyr Met Leu Gly
    130                 135                 140

Thr Gln Ala Phe Tyr Asp Ile Pro Ser Leu Gln Pro Ala Ala Pro Phe
145                 150                 155                 160

Asn Asn Pro Ala Trp Tyr His His Asn Gly Asp Ile Asn Trp Ser Leu
                165                 170                 175

Ala Asp Gly Arg Tyr Asp Gln Trp Ala Gln Asp Tyr Leu Glu Asn His
            180                 185                 190

Asp Leu Gly Gly Leu Asp Asp Ile Asp Phe Asp Val Pro Ala Ala Lys
        195                 200                 205

Gln Ala Ile Phe Ser Ser Ile Lys Gly Trp Phe Asp Tyr Thr Gly Ala
    210                 215                 220

Asp Gly Ala Arg Val Asp Ala Ala Lys Leu Met Lys Pro Thr Asp Ile
225                 230                 235                 240

Gly Glu Leu Gln Asn Leu Leu Gly Val Asn Thr Phe Gly Glu Asn Phe
                245                 250                 255

Asp Gly Asn Ala Glu Phe Val Ser Arg Trp Val Gly Thr Asn Lys Glu
            260                 265                 270

Trp Gly Met Leu Asp Phe Pro Leu Phe Phe Ser Val Leu Asn Ser Phe
        275                 280                 285
```

-continued

```
Ala Tyr Gly Gln Ser Phe Asp Ala Asn Ile Lys Gly Thr Leu Ala Gln
290                 295                 300

Asp Ser Tyr Tyr Gly Gly Asn Ala Asn His Met Val Thr Phe Ile Asp
305                 310                 315                 320

Asn His Asp Arg Asn Arg Phe Leu Thr Glu Ala Gly Gly Ser Val Glu
            325                 330                 335

Lys Leu Gln Asn Ala Leu Ser Phe Ile Phe Thr Val Arg Gly Thr Pro
            340                 345                 350

Val Val Phe Gln Gly Thr Glu Gln Asn Lys Gly Asn Gly Asn Gly Gln
        355                 360                 365

Ile Met Thr Gly Gly Ile Ala Asp Thr Trp Asn Arg Trp Ser Met Val
370                 375                 380

Lys Arg Asp Ala Asn Gly Asn Val Leu Glu Asn Tyr Phe Asn Glu Asn
385                 390                 395                 400

Ala Ser Thr Phe Lys His Val Ala Lys Leu Asn Glu Ile Arg Lys Asn
                405                 410                 415

Asn Pro Ala Leu Arg Thr Gly Thr Gln Arg Glu Met Trp Ser Ala Gln
            420                 425                 430

Asn Leu Tyr Ala Phe Ser Arg Arg Ile Asp Thr Gly Thr Asn Val Gly
        435                 440                 445

Gln Glu Val Ile Ser Ala Phe Ser Asn Ala Ser Gly Ser Gln Thr
450                 455                 460

Val Thr Leu Pro Leu Arg Ala Glu Ser Thr Leu Thr Ala Gly Thr Val
465                 470                 475                 480

Leu Val Asn Gln Leu Asn Pro Ser Asp Thr Val Thr Val Gln Ala Gly
                485                 490                 495

Gly Val Thr Gly Lys Gln Ile Thr Val Thr Leu Gly Ala Asn Ser Ala
            500                 505                 510

Lys Ile Tyr Ala Lys Thr Gln Pro Val Thr Asp Thr Gln Ala Pro Ser
        515                 520                 525

Val Pro Gly Asn Val Thr Ala Thr Val Gln Asn Ala Ser Ser Ala Leu
530                 535                 540

Val Ser Trp Ser Ala Ser Thr Asp Asn Val Gly Val Thr Gly Tyr Glu
545                 550                 555                 560

Ile Tyr Arg Asn Gly Val Lys Ile Gly Thr Ser Ala Thr Thr Ser Phe
                565                 570                 575

Thr Asp Asn Gly Leu Val Gly Ser Thr Asn Tyr Ser Tyr Thr Val Lys
            580                 585                 590

Ala Tyr Asp Ala Ala Met Asn Leu Ser Ala Phe Ser Ala Ala Ala Leu
        595                 600                 605

Ile Val Thr Pro Ala Gly Asn Ser Val Thr Ile Tyr Tyr Lys Gln Gly
610                 615                 620

Tyr Thr Asn Pro Tyr Ile His Tyr Arg Pro Val Gly Gly Thr Trp Thr
625                 630                 635                 640

Thr Ser Pro Gly Val Ala Ile Pro Ala Glu Val Ala Gly Tyr Asn
                645                 650                 655

Lys Ile Thr Ile Asn Ile Gly Ala Ala Thr Gln Leu Glu Ala Cys Phe
            660                 665                 670

Asn Asn Gly Ser Gly Ile Trp Asp Ser Asn Gly Ser Asn Tyr Leu
        675                 680                 685

Phe Gly Thr Gly Thr Trp Thr Tyr Thr Pro Thr Gly Asn Ile Gln Ala
690                 695                 700
```

```
Gly Gly Pro Val Thr Pro Thr Ala Ser Pro Thr Ala Thr Pro Thr Val
705                 710                 715                 720

Ala Pro Thr Ala Thr Pro Thr Val Thr Pro Thr Pro Thr Pro Thr Ala
                725                 730                 735

Thr Pro Thr Val Ala Pro Thr Ala Thr Pro Thr Val Ala Pro Thr Ala
            740                 745                 750

Thr Pro Val Pro Thr Ala Thr Pro Ala Gly Asn Thr Ala Thr Ile Tyr
        755                 760                 765

Tyr Lys Asn Thr Ala Phe Ser Asn Ser Tyr Ile His Tyr Lys Leu Asp
    770                 775                 780

Gly Ala Thr Thr Trp Thr Ser Pro Gly Val Pro Met Gln Ala Ser
785                 790                 795                 800

Thr Phe Ser Gly Tyr Lys Ser Ile Thr Ile Pro Leu Gly Thr Ala Thr
                805                 810                 815

Gly Leu Thr Ala Ala Phe Asn Asn Gly Ser Gly Thr Trp Asp Ser Asn
            820                 825                 830

Gly Gly Asn Asn Tyr His Phe Gly Thr Gly Ser Ser Ser Leu Val Gly
        835                 840                 845

Gly Ser Leu Thr Thr Gly Glu Pro Gln Ala Asp Ser Val Thr Phe Arg
850                 855                 860

Val Ser Val Pro Gly Ser Thr Pro Ala Asn Ala Pro Val Tyr Leu Thr
865                 870                 875                 880

Gly Ser Phe Asn Ser Trp Asn Ala Ala Asp Thr Ala Tyr Leu Leu Thr
                885                 890                 895

Arg Gly Ser Asp Gly Val Tyr Ser Val Thr Leu Asn Leu Pro Ala Gly
            900                 905                 910

Thr Ala Val Thr Tyr Lys Leu Thr Arg Gly Ser Trp Ala Thr Val Glu
        915                 920                 925

Thr Thr Ser Ser Gly Ala Asp Ile Thr Asn Arg Thr Leu Thr Pro Ala
930                 935                 940

Gly Gly Ala Gln Thr Val Thr Ile Ser Val Gln Arg Trp Lys Asp Gln
945                 950                 955                 960
```

<210> SEQ ID NO 3
<211> LENGTH: 2880
<212> TYPE: DNA
<213> ORGANISM: Bacillus circulans

<400> SEQUENCE: 3

```
gcgagtattg gtacagtaac cgagaatgac acgatctatc agattatggt tgaccgcttc      60
aatgacgggg attcttccaa taacgcaaca ggagctgcca tccgctatgg ggagaactct     120
gaggaggatt tccgttacat gaagggcggc gactggcagg gggtcattga caagctcccg     180
tatattcaca atatgggcta tactgcgatc tggatctcgc ccgtagccga gccgcagatg     240
actaaccgtg agaacaacgg aacaggcaag aacactgcct accacggcta caatgtcaaa     300
gatccgaaca aggccaaccc ttacttcggc accaagaaa agctgaaaga gcttgtagac     360
tccgcgcatc gctcggaat taaggtcatc attgatgtcg ttcccaacca catcggcgat     420
tacatgctgg gcactcaggc tttttacgat atcccatcct gcagcctgc cgctccgttc     480 aataatccgg cctggtatca ccacaatggg acattaact ggtcgcttgc cgatggacgg     540
tacgatcagt gggctcagga ttatctggag aatcatgatc tgggtggtct ggatgatatc     600
gacttcgatg ttcctgccgc caagcaggct attttcagct cgatcaaggg ctggtttgac     660
tatacggggg cagacggcgc ccgtgttgat gcggccaagc tgatgaagcc gaccgatatc     720
```

-continued

```
ggcgagctgc agaatttgct gggcgtgaat acgtttgggg agaatttcga cggcaatgcc    780
gaattcgtct cccgctgggt cggtaccaac aaggagtggg ggatgctcga cttcccgtta    840
ttcttctccg tgctgaacag cttcgcgtac gggcagtctt ttgacgcgaa tattaaaggc    900
actctggctc aagactccta ctacggcggc aacgccaacc atatggttac cttcatcgac    960
aatcatgacc gcaaccgctt cctgacgag gccggggca gtgtagagaa gctgcagaat     1020
gcgttgtcct ttattttcac cgtgcgcgga acgcctgtcg tcttccaggg aaccgagcag   1080
aacaagggca acggcaacgg gcagatcatg acgggcggga tcgccgatac gtggaaccgc   1140
tggtcgatgg tgaagcggga tgcaaacggc aatgtgctgg agaattattt caatgagaat   1200
gctagtacct tcaagcatgt agccaagctg aacgagatcc gcaaaaataa cccggccctg   1260
cgcaccggca cccagcgcga aatgtggtcc gcacagaatc tgtatgcctt ctcccggcgg   1320
attgataccg gcacgaatgt cggccaggaa gtgatctccg cattcagtaa tgcgtctggg   1380
ggatcacaga cagtgacgct gccgctgcgc gccgaaagca cgcttaccgc aggtacggtt   1440
ctggtgaatc agctgaaccc ctccgatact gtgaccgtgc aggcgggcgg tgttaccggt   1500
aagcaaatta cagttaccct aggcgccaat tcggccaaaa tctacgccaa acacaaccg    1560
gtaaccgata cgcaagcacc aagtgttccc ggaaatgtaa cagccaccgt acagaatgcc   1620
tccagcgcgt tggtatcctg gtcagcatcc accgataatg tcggggtgac tgggtatgaa   1680
atttaccgca atggagtgaa gatcggaact tcggcaacga cctcttttac agataacgga   1740
ctggtaggca gcaccaatta ttcttatacg gtaaaagcgt atgatgccgc catgaatctg   1800
tcggccttca gcgcagccgc cctgattgtc acccctgccg gtaacagtgt gacgatctac   1860
tacaagcagg gttacaccaa tccgtacatt cattaccgcc cggtgggcgg gacttggacg   1920
acatctccgg gtgtagccat tccagccgcc gaagtagcag gctataacaa aatcacaatc   1980
aatatcggcg cagccacgca gctcgaagcc tgcttcaaca acggcagcgg catctgggac   2040
agcaacggcg gcagcaatta cctgttcggg acaggcactt ggaccctatac gcctacaggc   2100
aatattcagg caggcggtcc ggtgacgcca acagcatcgc cgacggcgac accaaccgta   2160
gccccaacgg ctacaccgac cgtgacacca acaccaactc caacggctac accgaccgta   2220
gctccaaccg caacaccaac cgttgcgcca acggcgcac ctgtgccaac cgccactccg    2280
gcgggcaaca ccgcgacgat ctattacaag aatacagcat tcagtaactc gtatatccat   2340
tacaagctgg atggggcaac cacctggacg acctcaccgg gagtgcctat gcaggcctca   2400
accttcagcg gctacaagtc cattaccatt ccgctcggca ctgcaaccgg attgaccgca   2460
gcgttcaata cggcagcgg cacttgggac agcaatggcg ggaataacta tcatttcggt    2520
actggcagct ccagcctggt aggggggagc ttaaccacag gggaaccgca agcagacagc   2580
gtgaccttcc gggtcagcgt tcccgggtcc acccccgcga atgctccagt ctacctgaca   2640
ggatcgttca acagctggaa tgcggcagat acggcctacc tgctgacccg cggaagtgat   2700
ggcgtctatt ccgtcacctt gaatcttccg gcaggcactg ctgtaacgta taagctgaca   2760
cgtggaagct gggctacggt agagaccaca tccagcggcg cggatattac caaccggacg   2820
ctcacgcccg caggcggagc acagaccgtg acaataagtg tgcagcgctg gaaggatcag   2880
```

<210> SEQ ID NO 4
<211> LENGTH: 10
<212> TYPE: PRT
<213> ORGANISM: Bacillus circulans

```
<400> SEQUENCE: 4

Asn Thr Ala Tyr His Gly Tyr Asn Val Lys
1               5                   10

<210> SEQ ID NO 5
<211> LENGTH: 10
<212> TYPE: PRT
<213> ORGANISM: Bacillus circulans

<400> SEQUENCE: 5

Ala Asn Pro Tyr Phe Gly Thr Lys Glu Lys
1               5                   10

<210> SEQ ID NO 6
<211> LENGTH: 10
<212> TYPE: PRT
<213> ORGANISM: Bacillus circulans

<400> SEQUENCE: 6

Gly Gly Asp Trp Gln Gly Val Ile Asp Lys
1               5                   10

<210> SEQ ID NO 7
<211> LENGTH: 12
<212> TYPE: PRT
<213> ORGANISM: Bacillus circulans

<400> SEQUENCE: 7

Glu Leu Val Asp Ser Ala His Ala Leu Gly Ile Lys
1               5                   10

<210> SEQ ID NO 8
<211> LENGTH: 11
<212> TYPE: PRT
<213> ORGANISM: Bacillus circulans

<400> SEQUENCE: 8

Asn Thr Ala Phe Ser Asn Ser Tyr Ile His Tyr
1               5                   10

<210> SEQ ID NO 9
<211> LENGTH: 15
<212> TYPE: PRT
<213> ORGANISM: Bacillus circulans

<400> SEQUENCE: 9

Asp Thr Ala Tyr Leu Leu Thr Arg Gly Ser Asp Gly Val Tyr Ser
1               5                   10                  15

<210> SEQ ID NO 10
<211> LENGTH: 14
<212> TYPE: PRT
<213> ORGANISM: Bacillus circulans

<400> SEQUENCE: 10

Leu Pro Tyr Ile His Asn Met Gly Tyr Thr Ala Ile Trp Ile
1               5                   10

<210> SEQ ID NO 11
<211> LENGTH: 13
<212> TYPE: PRT
<213> ORGANISM: Bacillus circulans

<400> SEQUENCE: 11
```

```
Asp Ile Pro Ser Leu Gln Pro Ala Ala Pro Phe Asn Asn
1               5                   10
```

<210> SEQ ID NO 12
<211> LENGTH: 15
<212> TYPE: PRT
<213> ORGANISM: Bacillus circulans

<400> SEQUENCE: 12

```
Pro Thr Asp Ile Gly Glu Leu Gln Asn Leu Leu Gly Val Asn Thr
1               5                   10                  15
```

<210> SEQ ID NO 13
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is a, c, g, or t

<400> SEQUENCE: 13
gayacnatht aycarat                                                17

<210> SEQ ID NO 14
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (15)..(15)
<223> OTHER INFORMATION: n is a, c, g, or t

<400> SEQUENCE: 14
taycaratha tggtnga                                                17

<210> SEQ ID NO 15
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (9)..(9)
<223> OTHER INFORMATION: n is a, c, g, or t

<400> SEQUENCE: 15
acrttrtanc crtgrta                                                17

<210> SEQ ID NO 16
<211> LENGTH: 17
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 16

```
ccrtgrtang cngtrtt                                             17

<210> SEQ ID NO 17
<211> LENGTH: 251
<212> TYPE: DNA
<213> ORGANISM: Bacillus circulans

<400> SEQUENCE: 17 tat cag att atg gtt gac cgc ttc aat gac ggg gat tct tcc aat aac    48
Tyr Gln Ile Met Val Asp Arg Phe Asn Asp Gly Asp Ser Ser Asn Asn
  1               5                  10                  15 gca aca gga gct gcc atc cgc tat ggg gag aac tct gag gag gat ttc    96
Ala Thr Gly Ala Ala Ile Arg Tyr Gly Glu Asn Ser Glu Glu Asp Phe
             20                  25                  30 cgt tac atg aag ggc ggc gac tgg cag ggg gtc att gac aag ctc ccg   144
Arg Tyr Met Lys Gly Gly Asp Trp Gln Gly Val Ile Asp Lys Leu Pro
         35                  40                  45 tat att cac aat atg ggc tat act gcg atc tgg atc tcg ccc gta gcc   192
Tyr Ile His Asn Met Gly Tyr Thr Ala Ile Trp Ile Ser Pro Val Ala
     50                  55                  60 gag ccg cag atg act aac cgt gag aac aac gga aca ggc aag aac act   240
Glu Pro Gln Met Thr Asn Arg Glu Asn Asn Gly Thr Gly Lys Asn Thr
 65                  70                  75                  80 gcc tac cac gg                                                    251
Ala Tyr His <210> SEQ ID NO 18
<211> LENGTH: 2985
<212> TYPE: DNA
<213> ORGANISM: Bacillus circulans

<400> SEQUENCE: 18 atg aaa aga gaa cgt aac cgc cta ctt att ccc gtt cta atc gca tcc    48
Met Lys Arg Glu Arg Asn Arg Leu Leu Ile Pro Val Leu Ile Ala Ser
  1               5                  10                  15 att gta ctg tct atc acg atg agt ctg ttt gtt gta ccg cct tct aag    96
Ile Val Leu Ser Ile Thr Met Ser Leu Phe Val Val Pro Pro Ser Lys
             20                  25                  30 gcg gag gct gcg agt att ggt aca gta acc gag aat gac acg atc tat   144
Ala Glu Ala Ala Ser Ile Gly Thr Val Thr Glu Asn Asp Thr Ile Tyr
         35                  40                  45 cag att atg gtt gac cgc ttc aat gac ggg gat tct tcc aat aac gca   192
Gln Ile Met Val Asp Arg Phe Asn Asp Gly Asp Ser Ser Asn Asn Ala
     50                  55                  60 aca gga gct gcc atc cgc tat ggg gag aac tct gag gag gat ttc cgt   240
Thr Gly Ala Ala Ile Arg Tyr Gly Glu Asn Ser Glu Glu Asp Phe Arg
 65                  70                  75                  80 tac atg aag ggc ggc gac tgg cag ggg gtc att gac aag ctc ccg tat   288
Tyr Met Lys Gly Gly Asp Trp Gln Gly Val Ile Asp Lys Leu Pro Tyr
                 85                  90                  95 att cac aat atg ggc tat act gcg atc tgg atc tcg ccc gta gcc gag   336
Ile His Asn Met Gly Tyr Thr Ala Ile Trp Ile Ser Pro Val Ala Glu
            100                 105                 110 ccg cag atg act aac cgt gag aac aac gga aca ggc aag aac act gcc   384
Pro Gln Met Thr Asn Arg Glu Asn Asn Gly Thr Gly Lys Asn Thr Ala
        115                 120                 125 tac cac ggc tac aat gtc aaa gat ccg aac aag gcc aac cct tac ttc   432
Tyr His Gly Tyr Asn Val Lys Asp Pro Asn Lys Ala Asn Pro Tyr Phe
    130                 135                 140 ggc acc aaa gaa aag ctg aaa gag ctt gta gac tcc gcg cat gcg ctc   480
```

```
Gly Thr Lys Glu Lys Leu Lys Glu Leu Val Asp Ser Ala His Ala Leu
145                 150                 155                 160 gga att aag gtc atc att gat gtc gtt ccc aac cac atc ggc gat tac       528
Gly Ile Lys Val Ile Ile Asp Val Val Pro Asn His Ile Gly Asp Tyr
                165                 170                 175 atg ctg ggc act cag gct ttt tac gat atc cca tcc ttg cag cct gcc       576
Met Leu Gly Thr Gln Ala Phe Tyr Asp Ile Pro Ser Leu Gln Pro Ala
            180                 185                 190 gct ccg ttc aat aat ccg gcc tgg tat cac cac aat ggg gac att aac       624
Ala Pro Phe Asn Asn Pro Ala Trp Tyr His His Asn Gly Asp Ile Asn
        195                 200                 205 tgg tcg ctt gcc gat gga cgg tac gat cag tgg gct cag gat tat ctg       672
Trp Ser Leu Ala Asp Gly Arg Tyr Asp Gln Trp Ala Gln Asp Tyr Leu
    210                 215                 220 gag aat cat gat ctg ggt ggt ctg gat gat atc gac ttc gat gtt cct       720
Glu Asn His Asp Leu Gly Gly Leu Asp Asp Ile Asp Phe Asp Val Pro
225                 230                 235                 240 gcc gcc aag cag gct att ttc agc tcg atc aag ggc tgg ttt gac tat       768
Ala Ala Lys Gln Ala Ile Phe Ser Ser Ile Lys Gly Trp Phe Asp Tyr
                245                 250                 255 acg ggg gca gac ggc gcc cgt gtt gat gcg gcc aag ctg atg aag ccg       816
Thr Gly Ala Asp Gly Ala Arg Val Asp Ala Ala Lys Leu Met Lys Pro
            260                 265                 270 acc gat atc ggc gag ctg cag aat ttg ctg ggc gtg aat acg ttt ggg       864
Thr Asp Ile Gly Glu Leu Gln Asn Leu Leu Gly Val Asn Thr Phe Gly
        275                 280                 285 gag aat ttc gac ggc aat gcc gaa ttc gtc tcc cgc tgg gtc ggt acc       912
Glu Asn Phe Asp Gly Asn Ala Glu Phe Val Ser Arg Trp Val Gly Thr
    290                 295                 300 aac aag gag tgg ggg atg ctc gac ttc ccg tta ttc ttc tcc gtg ctg       960
Asn Lys Glu Trp Gly Met Leu Asp Phe Pro Leu Phe Phe Ser Val Leu
305                 310                 315                 320 aac agc ttc gcg tac ggg cag tct ttt gac gcg aat att aaa ggc act      1008
Asn Ser Phe Ala Tyr Gly Gln Ser Phe Asp Ala Asn Ile Lys Gly Thr
                325                 330                 335 ctg gct caa gac tcc tac tac ggc ggc aac gcc aac cat atg gtt acc      1056
Leu Ala Gln Asp Ser Tyr Tyr Gly Gly Asn Ala Asn His Met Val Thr
            340                 345                 350 ttc atc gac aat cat gac cgc aac cgc ttc ctg acg gag gcc ggg ggc      1104
Phe Ile Asp Asn His Asp Arg Asn Arg Phe Leu Thr Glu Ala Gly Gly
        355                 360                 365 agt gta gag aag ctg cag aat gcg ttg tcc ttt att ttc acc gtg cgc      1152
Ser Val Glu Lys Leu Gln Asn Ala Leu Ser Phe Ile Phe Thr Val Arg
    370                 375                 380 gga acg cct gtc gtc ttc cag gga acc gag cag aac aag ggc aac ggc      1200
Gly Thr Pro Val Val Phe Gln Gly Thr Glu Gln Asn Lys Gly Asn Gly
385                 390                 395                 400 aac ggg cag atc atg acg ggc ggg atc gcc gat acg tgg aac cgc tgg      1248
Asn Gly Gln Ile Met Thr Gly Gly Ile Ala Asp Thr Trp Asn Arg Trp
                405                 410                 415 tcg atg gtg aag cgg gat gca aac ggc aat gtg ctg gag aat tat ttc      1296
Ser Met Val Lys Arg Asp Ala Asn Gly Asn Val Leu Glu Asn Tyr Phe
            420                 425                 430 aat gag aat gct agt acc ttc aag cat gta gcc aag ctg aac gag atc      1344
Asn Glu Asn Ala Ser Thr Phe Lys His Val Ala Lys Leu Asn Glu Ile
        435                 440                 445 cgc aaa aat aac ccg gcc ctg cgc acc ggc acc cag cgc gaa atg tgg      1392
Arg Lys Asn Asn Pro Ala Leu Arg Thr Gly Thr Gln Arg Glu Met Trp
    450                 455                 460
```

```
tcc gca cag aat ctg tat gcc ttc tcc cgg cgg att gat acc ggc acg       1440
Ser Ala Gln Asn Leu Tyr Ala Phe Ser Arg Arg Ile Asp Thr Gly Thr
465                 470                 475                 480 aat gtc ggc cag gaa gtg atc tcc gca ttc agt aat gcg tct ggg gga       1488
Asn Val Gly Gln Glu Val Ile Ser Ala Phe Ser Asn Ala Ser Gly Gly
                485                 490                 495 tca cag aca gtg acg ctg ccg ctg cgc gcc gaa agc acg ctt acc gca       1536
Ser Gln Thr Val Thr Leu Pro Leu Arg Ala Glu Ser Thr Leu Thr Ala
        500                 505                 510 ggt acg gtt ctg gtg aat cag ctg aac ccc tcc gat act gtg acc gtg       1584
Gly Thr Val Leu Val Asn Gln Leu Asn Pro Ser Asp Thr Val Thr Val
    515                 520                 525 cag gcg ggc ggt gtt acc ggt aag caa att aca gtt acc cta ggc gcc       1632
Gln Ala Gly Gly Val Thr Gly Lys Gln Ile Thr Val Thr Leu Gly Ala
530                 535                 540 aat tcg gcc aaa atc tac gcc aaa aca caa ccg gta acc gat acg caa       1680
Asn Ser Ala Lys Ile Tyr Ala Lys Thr Gln Pro Val Thr Asp Thr Gln
545                 550                 555                 560 gca cca agt gtt ccc gga aat gta aca gcc acc gta cag aat gcc tcc       1728
Ala Pro Ser Val Pro Gly Asn Val Thr Ala Thr Val Gln Asn Ala Ser
                565                 570                 575 agc gcg ttg gta tcc tgg tca gca tcc acc gat aat gtc ggg gtg act       1776
Ser Ala Leu Val Ser Trp Ser Ala Ser Thr Asp Asn Val Gly Val Thr
        580                 585                 590 ggg tat gaa att tac cgc aat gga gtg aag atc gga act tcg gca acg       1824
Gly Tyr Glu Ile Tyr Arg Asn Gly Val Lys Ile Gly Thr Ser Ala Thr
    595                 600                 605 acc tct ttt aca gat aac gga ctg gta ggc agc acc aat tat tct tat       1872
Thr Ser Phe Thr Asp Asn Gly Leu Val Gly Ser Thr Asn Tyr Ser Tyr
610                 615                 620 acg gta aaa gcg tat gat gcc gcc atg aat ctg tcg gcc ttc agc gca       1920
Thr Val Lys Ala Tyr Asp Ala Ala Met Asn Leu Ser Ala Phe Ser Ala
625                 630                 635                 640 gcc gcc ctg att gtc acc cct gcc ggt aac agt gtg acg atc tac tac       1968
Ala Ala Leu Ile Val Thr Pro Ala Gly Asn Ser Val Thr Ile Tyr Tyr
                645                 650                 655 aag cag ggt tac acc aat ccg tac att cat tac cgc ccg gtg ggc ggg       2016
Lys Gln Gly Tyr Thr Asn Pro Tyr Ile His Tyr Arg Pro Val Gly Gly
        660                 665                 670 act tgg acg aca tct ccg ggt gta gcc att cca gcc gcc gaa gta gca       2064
Thr Trp Thr Thr Ser Pro Gly Val Ala Ile Pro Ala Ala Glu Val Ala
    675                 680                 685 ggc tat aac aaa atc aca atc aat atc ggc gca gcc acg cag ctc gaa       2112
Gly Tyr Asn Lys Ile Thr Ile Asn Ile Gly Ala Ala Thr Gln Leu Glu
690                 695                 700 gcc tgc ttc aac aac ggc agc ggc atc tgg gac agc aac ggc ggc agc       2160
Ala Cys Phe Asn Asn Gly Ser Gly Ile Trp Asp Ser Asn Gly Gly Ser
705                 710                 715                 720 aat tac ctg ttc ggg aca ggc act tgg acc tat acg cct aca ggc aat       2208
Asn Tyr Leu Phe Gly Thr Gly Thr Trp Thr Tyr Thr Pro Thr Gly Asn
                725                 730                 735 att cag gca ggc ggt ccg gtg acg cca aca gca tcg ccg acg gcg aca       2256
Ile Gln Ala Gly Gly Pro Val Thr Pro Thr Ala Ser Pro Thr Ala Thr
        740                 745                 750 cca acc gta gcc cca acg gct aca ccg acc gtg aca cca aca cca act       2304
Pro Thr Val Ala Pro Thr Ala Thr Pro Thr Val Thr Pro Thr Pro Thr
    755                 760                 765 cca acg gct aca ccg acc gta gct cca acc gca aca cca acc gtt gcg       2352
Pro Thr Ala Thr Pro Thr Val Ala Pro Thr Ala Thr Pro Thr Val Ala
770                 775                 780
```

```
cca acg gcg aca cct gtg cca acc gcc act ccg gcg ggc aac acc gcg    2400
Pro Thr Ala Thr Pro Val Pro Thr Ala Thr Pro Ala Gly Asn Thr Ala
785                 790                 795                 800 acg atc tat tac aag aat aca gca ttc agt aac tcg tat atc cat tac    2448
Thr Ile Tyr Tyr Lys Asn Thr Ala Phe Ser Asn Ser Tyr Ile His Tyr
                805                 810                 815 aag ctg gat ggg gca acc acc tgg acg acc tca ccg gga gtg cct atg    2496
Lys Leu Asp Gly Ala Thr Thr Trp Thr Thr Ser Pro Gly Val Pro Met
            820                 825                 830 cag gcc tca acc ttc agc ggc tac aag tcc att acc att ccg ctc ggc    2544
Gln Ala Ser Thr Phe Ser Gly Tyr Lys Ser Ile Thr Ile Pro Leu Gly
        835                 840                 845 act gca acc gga ttg acc gca gcg ttc aat aac ggc agc ggc act tgg    2592
Thr Ala Thr Gly Leu Thr Ala Ala Phe Asn Asn Gly Ser Gly Thr Trp
850                 855                 860 gac agc aat ggc ggg aat aac tat cat ttc ggt act ggc agc tcc agc    2640
Asp Ser Asn Gly Gly Asn Asn Tyr His Phe Gly Thr Gly Ser Ser Ser
865                 870                 875                 880 ctg gta ggg ggg agc tta acc aca ggg gaa ccg caa gca gac agc gtg    2688
Leu Val Gly Gly Ser Leu Thr Thr Gly Glu Pro Gln Ala Asp Ser Val
                885                 890                 895 acc ttc cgg gtc agc gtt ccc ggg tcc acc ccg gcg aat gct cca gtc    2736
Thr Phe Arg Val Ser Val Pro Gly Ser Thr Pro Ala Asn Ala Pro Val
            900                 905                 910 tac ctg aca gga tcg ttc aac agc tgg aat gcg gca gat acg gcc tac    2784
Tyr Leu Thr Gly Ser Phe Asn Ser Trp Asn Ala Ala Asp Thr Ala Tyr
        915                 920                 925 ctg ctg acc cgc gga agt gat ggc gtc tat tcc gtc acc ttg aat ctt    2832
Leu Leu Thr Arg Gly Ser Asp Gly Val Tyr Ser Val Thr Leu Asn Leu
930                 935                 940 ccg gca ggc act gct gta acg tat aag ctg aca cgt gga agc tgg gct    2880
Pro Ala Gly Thr Ala Val Thr Tyr Lys Leu Thr Arg Gly Ser Trp Ala
945                 950                 955                 960 acg gta gag acc aca tcc agc ggc gcg gat att acc aac cgg acg ctc    2928
Thr Val Glu Thr Thr Ser Ser Gly Ala Asp Ile Thr Asn Arg Thr Leu
                965                 970                 975 acg ccc gca ggc gga gca cag acc gtg aca ata agt gtg cag cgc tgg    2976
Thr Pro Ala Gly Gly Ala Gln Thr Val Thr Ile Ser Val Gln Arg Trp
            980                 985                 990 aag gat cag                                                         2985
Lys Asp Gln
        995

<210> SEQ ID NO 19
<211> LENGTH: 22
<212> TYPE: DNA
<213> ORGANISM: Artificial Sequence
<220> FEATURE:
<223> OTHER INFORMATION: synthetic

<400> SEQUENCE: 19
gcaattaacc ctcactaaag gg                                              22

<210> SEQ ID NO 20
<211> LENGTH: 30
<212> TYPE: DNA
<213> ORGANISM: Artificial Sequence
<220> FEATURE:
<223> OTHER INFORMATION: synthetic

<400> SEQUENCE: 20
```

-continued

```
aaaaacatat gaaaagagaa cgtaaccgcc                                    30

<210> SEQ ID NO 21
<211> LENGTH: 30
<212> TYPE: DNA
<213> ORGANISM: Artificial Sequence
<220> FEATURE:
<223> OTHER INFORMATION: synthetic

<400> SEQUENCE: 21
cggcaacgcc aaccacatgg ttaccttcat                                    30

<210> SEQ ID NO 22
<211> LENGTH: 30
<212> TYPE: DNA
<213> ORGANISM: Artificial Sequence
<220> FEATURE:
<223> OTHER INFORMATION: synthetic

<400> SEQUENCE: 22
atgaaggtaa ccatgtggtt ggcgttgccg                                    30

<210> SEQ ID NO 23
<211> LENGTH: 30
<212> TYPE: DNA
<213> ORGANISM: Artificial Sequence
<220> FEATURE:
<223> OTHER INFORMATION: synthetic

<400> SEQUENCE: 23
aaaaaggatc cttactgatc cttccagcgc                                    30
```